US010159644B2

(12) United States Patent
Smutney et al.

(10) Patent No.: US 10,159,644 B2
(45) Date of Patent: Dec. 25, 2018

(54) INHALABLE VACCINE COMPOSITIONS AND METHODS

(71) Applicants: MannKind Corporation, Valencia, CA (US); TechnoVax Inc., Tarrytown, NY (US)

(72) Inventors: Chad C. Smutney, Watertown, CT (US); Andrea Leone-Bay, Ridgefield, CT (US); Jose M. Galarza, Scarsdale, NY (US); Hector Munoz, Scarsdale, NY (US); George R. Martin, Rockville, MD (US); Marshall L. Grant, Newtown, CT (US)

(73) Assignees: MannKind Corporation, Westlake Village, CA (US); Technovax, Inc., Tarrytown, NY (US)

( * ) Notice: Subject to any disclaimer, the term of this patent is extended or adjusted under 35 U.S.C. 154(b) by 613 days.

(21) Appl. No.: 14/438,582

(22) PCT Filed: Oct. 25, 2013

(86) PCT No.: PCT/US2013/066969
§ 371 (c)(1),
(2) Date: Apr. 24, 2015

(87) PCT Pub. No.: WO2014/066856
PCT Pub. Date: May 1, 2014

(65) Prior Publication Data
US 2015/0283069 A1    Oct. 8, 2015

Related U.S. Application Data

(60) Provisional application No. 61/719,308, filed on Oct. 26, 2012.

(51) Int. Cl.
| *A61K 45/06*  | (2006.01) |
| *A61K 31/4985* | (2006.01) |
| *A61K 31/519* | (2006.01) |
| *C07D 471/04* | (2006.01) |
| *A61K 31/5377* | (2006.01) |
| *A61K 9/00* | (2006.01) |
| *A61K 39/12* | (2006.01) |
| *A61K 39/145* | (2006.01) |
| *A61K 39/07* | (2006.01) |
| *A61M 15/00* | (2006.01) |
| *A61K 47/22* | (2006.01) |
| *C12N 7/00* | (2006.01) |
| *A61K 39/00* | (2006.01) |

(52) U.S. Cl.
CPC ............ *A61K 9/0075* (2013.01); *A61K 39/07* (2013.01); *A61K 39/12* (2013.01); *A61K 39/145* (2013.01); *A61K 47/22* (2013.01); *A61M 15/003* (2014.02); *A61M 15/0021* (2014.02); *C12N 7/00* (2013.01); *A61K 2039/525* (2013.01); *A61K 2039/544* (2013.01); *A61K 2039/55555* (2013.01); *A61M 2202/064* (2013.01); *C12N 2760/16134* (2013.01)

(58) Field of Classification Search
CPC .. A61K 45/06; A61K 31/4985; A61K 31/519; A61K 31/5377; C07D 471/04
See application file for complete search history.

(56) References Cited

U.S. PATENT DOCUMENTS

| 2,549,303 | A | 4/1951 | Friden |
| 2,754,276 | A | 7/1956 | Joseph et al. |
| D189,076 | S | 10/1960 | Altman |
| 3,337,740 | A | 8/1967 | Gray et al. |
| 3,407,203 | A | 10/1968 | Buijle |
| 3,518,340 | A | 6/1970 | Raper |
| 3,622,053 | A | 11/1971 | Ryden |
| 3,673,698 | A | 7/1972 | Guerard |
| 3,669,113 | A | 8/1972 | Altounyan et al. |
| 3,823,816 | A | 7/1974 | Controullis et al. |
| 3,823,843 | A | 7/1974 | Stephens et al. |
| 3,856,142 | A | 12/1974 | Vessalo |
| 3,873,651 | A | 3/1975 | Mosley, Jr. et al. |

(Continued)

FOREIGN PATENT DOCUMENTS

| CA | 2536047 A1 | 3/2005 |
| CA | 2551182 C | 8/2010 |

(Continued)

OTHER PUBLICATIONS

Amorij et al. "Development of stable influenza vaccine powder formulations: challenges and possibilities", Pharmaceutical research, 2008, 25(6):1256-1273.*

(Continued)

*Primary Examiner* — Barry A Chestnut
(74) *Attorney, Agent, or Firm* — K&L Gates LLP; Louis C. Cullman; Hal Gibson

(57) ABSTRACT

Dry powder inhalable compositions and methods for using and making the compositions are disclosed for vaccinating a subject against disease. In particular, the compositions are inhalable dry powders useful for preventing and/or treating diseases caused by microorganisms, for example, microorganisms such as viral or bacterial pathogens, including, the influenza virus. In particular, the method comprises the administration of an inhalable composition comprising virus-like particles and/or specific protein/s or antigenic peptides, peptide fragments and/or derivatives thereof using a dry powder drug delivery system.

20 Claims, 2 Drawing Sheets

(56) References Cited

U.S. PATENT DOCUMENTS

| | | |
|---|---|---|
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,066,756 A | 1/1978 | Orr et al. |
| 4,078,128 A | 3/1978 | Hoyt et al. |
| 4,091,077 A | 5/1978 | Smith et al. |
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,168,002 A | 9/1979 | Crosby |
| 4,171,000 A | 10/1979 | Uhle |
| 4,175,556 A | 11/1979 | Freezer |
| 4,187,129 A | 2/1980 | Bost et al. |
| 4,196,196 A | 4/1980 | Tiholiz |
| 4,206,758 A | 6/1980 | Hallworth et al. |
| 4,210,140 A | 7/1980 | James et al. |
| 4,211,769 A | 7/1980 | Okada |
| 4,268,460 A | 5/1981 | Boiarski et al. |
| 4,272,398 A | 6/1981 | Jaffe |
| 4,275,820 A | 6/1981 | LeBlond |
| 4,289,759 A | 9/1981 | Heavener |
| 4,294,829 A | 10/1981 | Suzuki |
| 4,300,546 A | 11/1981 | Kruber |
| 4,356,167 A | 10/1982 | Kelly |
| D269,463 S | 6/1983 | Young et al. |
| 4,407,525 A | 10/1983 | Hoppe |
| 4,456,007 A | 6/1984 | Nakao et al. |
| 4,483,922 A | 11/1984 | Carpenter |
| D276,654 S | 12/1984 | Snellman-Wasenius et al. |
| 4,487,327 A | 12/1984 | Grayson |
| 4,524,769 A | 6/1985 | Wetterlin |
| 4,526,804 A | 7/1985 | Escallon |
| 4,534,345 A | 8/1985 | Wetterlin |
| D282,209 S | 1/1986 | Newell et al. |
| 4,581,020 A | 4/1986 | Mittleman |
| 4,592,348 A | 6/1986 | Waters, IV et al. |
| 4,613,500 A | 9/1986 | Suzuki |
| 4,615,817 A | 10/1986 | McCoy |
| 4,624,861 A | 11/1986 | Yale et al. |
| 4,637,996 A | 1/1987 | Konishi |
| D288,852 S | 3/1987 | Miyoshi |
| 4,659,696 A | 4/1987 | Hirai et al. |
| 4,668,218 A | 5/1987 | Virtanen |
| 4,681,752 A | 7/1987 | Melillo |
| D295,321 S | 4/1988 | Hallworth |
| 4,757,066 A | 7/1988 | Shiokari et al. |
| 4,792,451 A | 12/1988 | Kim |
| 4,811,731 A | 3/1989 | Newell et al. |
| D301,273 S | 5/1989 | Leonard |
| 4,835,312 A | 5/1989 | Itoh et al. |
| 4,841,964 A | 6/1989 | Hurka et al. |
| 4,847,091 A | 7/1989 | Illum |
| 4,849,227 A | 7/1989 | Cho |
| 4,861,627 A | 8/1989 | Mathiowitz |
| 4,866,051 A | 9/1989 | Hunt et al. |
| 4,873,087 A | 10/1989 | Morishita et al. |
| 4,887,722 A | 12/1989 | Greenward, Sr. |
| 4,900,730 A | 2/1990 | Miyauchi |
| 4,907,583 A | 3/1990 | Wetterlin et al. |
| 4,925,673 A | 5/1990 | Steiner |
| 4,926,852 A | 5/1990 | Zoltan et al. |
| 4,927,555 A | 5/1990 | Colarusso, Jr. |
| 4,927,928 A | 5/1990 | Shroot et al. |
| 4,946,828 A | 8/1990 | Markussen |
| 4,981,295 A | 1/1991 | Belman et al. |
| 4,981,625 A | 1/1991 | Rhim et al. |
| 4,983,402 A | 1/1991 | Steiner et al. |
| 4,984,158 A | 1/1991 | Hillsman |
| 4,991,605 A | 2/1991 | Keritsis |
| 4,998,624 A | 3/1991 | Capes et al. |
| 5,006,343 A | 4/1991 | Benson |
| D316,902 S | 5/1991 | Hoefling |
| 5,017,383 A | 5/1991 | Ozawa et al. |
| 5,019,400 A | 5/1991 | Gombotz et al. |
| 5,021,376 A | 6/1991 | Nienburg et al. |
| 5,027,806 A | 7/1991 | Zoltan et al. |
| 5,042,975 A | 8/1991 | Chien |
| D321,570 S | 11/1991 | Blasdell et al. |
| 5,067,500 A | 11/1991 | Keritsis |
| 5,069,204 A | 12/1991 | Smith et al. |
| 5,074,418 A | 12/1991 | Buan et al. |
| 5,075,027 A | 12/1991 | Dixit et al. |
| 5,098,590 A | 3/1992 | Dixit et al. |
| 5,105,291 A | 4/1992 | Matsumoto et al. |
| D326,517 S | 5/1992 | Funai et al. |
| 5,110,007 A | 5/1992 | Law et al. |
| 5,110,823 A | 5/1992 | Hamaguchi et al. |
| 5,118,666 A | 6/1992 | Habener |
| 5,120,712 A | 6/1992 | Habener |
| 5,124,291 A | 6/1992 | Bremer et al. |
| 5,131,539 A | 7/1992 | Karita et al. |
| 5,139,878 A | 8/1992 | Kim |
| 5,145,684 A | 9/1992 | Liversidge et al. |
| 5,152,284 A | 10/1992 | Valentini et al. |
| D331,106 S | 11/1992 | Fuchs |
| 5,167,506 A | 12/1992 | Kilis et al. |
| 5,170,801 A | 12/1992 | Casper et al. |
| 5,188,837 A | 2/1993 | Domb |
| 5,196,049 A | 3/1993 | Coombs et al. |
| 5,201,308 A | 4/1993 | Newhouse |
| 5,203,768 A | 4/1993 | Haak et al. |
| 5,204,108 A | 4/1993 | Ilium |
| 5,208,998 A | 5/1993 | Dyler, Jr. |
| 5,215,739 A | 6/1993 | Kamishita et al. |
| D337,636 S | 7/1993 | Kocinski |
| D338,062 S | 8/1993 | Yair |
| D338,268 S | 8/1993 | Kobayashi et al. |
| 5,239,992 A | 8/1993 | Bougamont et al. |
| 5,244,653 A | 9/1993 | Berke et al. |
| 5,250,287 A | 10/1993 | Cocozza |
| D340,975 S | 11/1993 | Sladek |
| 5,260,306 A | 11/1993 | Boardman et al. |
| 5,270,305 A | 12/1993 | Palmer |
| 5,287,850 A | 2/1994 | Haber et al. |
| D344,796 S | 3/1994 | Sochon et al. |
| D344,797 S | 3/1994 | Sochon et al. |
| D345,013 S | 3/1994 | Huck et al. |
| 5,301,666 A | 4/1994 | Lerk et al. |
| 5,306,453 A | 4/1994 | Shulman |
| D347,057 S | 5/1994 | Yair |
| D348,100 S | 6/1994 | Clarke |
| 5,320,094 A | 6/1994 | Laube et al. |
| D348,928 S | 7/1994 | Ashley et al. |
| D348,929 S | 7/1994 | Paton |
| 5,327,883 A | 7/1994 | Williams et al. |
| 5,328,464 A | 7/1994 | Kriesel et al. |
| 5,331,953 A | 7/1994 | Andersson et al. |
| 5,333,106 A | 7/1994 | Lanpher et al. |
| D349,572 S | 8/1994 | Jagnandan et al. |
| D350,193 S | 8/1994 | Huck et al. |
| 5,337,740 A | 8/1994 | Armstrong et al. |
| D350,602 S | 9/1994 | Hobbs et al. |
| D350,821 S | 9/1994 | Wright et al. |
| 5,351,683 A | 10/1994 | Chiesi et al. |
| 5,352,461 A | 10/1994 | Feldstein et al. |
| 5,354,562 A | 10/1994 | Platz |
| 5,358,734 A | 10/1994 | Lenox et al. |
| D352,107 S | 11/1994 | Meier et al. |
| 5,360,614 A | 11/1994 | Fox et al. |
| 5,363,842 A | 11/1994 | Mishelevich et al. |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |

(56) References Cited

U.S. PATENT DOCUMENTS

| | | |
|---|---|---|
| 5,394,868 A | 3/1995 | Ambrosio et al. |
| 5,401,516 A | 3/1995 | Milstein et al. |
| D357,603 S | 4/1995 | Wolff |
| 5,404,871 A | 4/1995 | Goodman et al. |
| D358,880 S | 5/1995 | Mulhauser et al. |
| 5,413,804 A | 5/1995 | Rhodes |
| 5,415,162 A | 5/1995 | Casper et al. |
| D359,153 S | 6/1995 | Viggiano |
| D359,555 S | 6/1995 | Funai et al. |
| 5,424,286 A | 6/1995 | Eng |
| 5,437,271 A | 8/1995 | Hodson et al. |
| 5,443,841 A | 8/1995 | Milstein et al. |
| D362,500 S | 9/1995 | Cook et al. |
| 5,447,150 A | 9/1995 | Bacon |
| 5,447,151 A | 9/1995 | Bruna et al. |
| 5,447,728 A | 9/1995 | Milstein et al. |
| 5,451,410 A | 9/1995 | Milstein et al. |
| D363,775 S | 10/1995 | Hobbs |
| 5,454,871 A | 10/1995 | Liaw et al. |
| 5,455,335 A | 10/1995 | Kahne et al. |
| 5,458,135 A | 10/1995 | Patton et al. |
| 5,469,750 A | 11/1995 | Lloyd et al. |
| 5,469,971 A | 11/1995 | Chilton et al. |
| 5,476,093 A | 12/1995 | Laniken |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar et al. |
| 5,483,954 A | 1/1996 | Mecikalski |
| 5,484,606 A | 1/1996 | Dhaber et al. |
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstorm et al. |
| D370,255 S | 5/1996 | Yamamoto et al. |
| 5,514,646 A | 5/1996 | Chance et al. |
| 5,518,998 A | 5/1996 | Backstorm et al. |
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,541,155 A | 7/1996 | Leone-Bay |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,615,670 A | 4/1997 | Rhodes et al. |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Yang |
| 5,634,900 A | 6/1997 | Makino et al. |
| 5,639,441 A | 6/1997 | Sievers et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstrom et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,727,333 A | 3/1998 | Folan |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton et al. |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A | 9/1998 | Wolf |
| 5,811,127 A | 9/1998 | Milstein et al. |
| 5,813,397 A | 9/1998 | Goodman et al. |
| 5,817,343 A | 10/1998 | Burke |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,868,774 A | 2/1999 | Reil |
| 5,874,064 A | 2/1999 | Edwards et al. |
| 5,875,776 A | 3/1999 | Vaghefi |
| 5,877,174 A | 3/1999 | Ono et al. |
| 5,881,719 A | 3/1999 | Gottenauer et al. |

(56) References Cited

U.S. PATENT DOCUMENTS

| | | |
|---|---|---|
| 5,881,721 A | 3/1999 | Bunce et al. |
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |
| 5,922,253 A | 7/1999 | Herbert et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,942,242 A | 8/1999 | Mizushima et al. |
| 5,972,242 A | 8/1999 | Mizushima et al. |
| 5,948,749 A | 9/1999 | Igarashi et al. |
| 5,952,008 A | 9/1999 | Backstrom et al. |
| 5,954,047 A | 9/1999 | Armer et al. |
| 5,965,701 A | 10/1999 | Junien |
| 5,971,951 A | 10/1999 | Ruskewicz |
| D416,085 S | 11/1999 | Forssell et al. |
| D416,621 S | 11/1999 | Forssell et al. |
| D416,998 S | 11/1999 | Hodson et al. |
| D417,271 S | 11/1999 | Denyer et al. |
| 5,975,347 A | 11/1999 | Lambelet, Jr. et al. |
| 5,976,569 A | 11/1999 | Milstein |
| 5,976,574 A | 11/1999 | Gordon |
| 5,977,071 A | 11/1999 | Galloway et al. |
| 5,980,865 A | 11/1999 | Ahmed et al. |
| 5,981,488 A | 11/1999 | Hoffman |
| 5,983,893 A | 11/1999 | Wetterlin |
| 5,985,248 A | 11/1999 | Gordon et al. |
| 5,985,309 A | 11/1999 | Edwards et al. |
| 5,990,077 A | 11/1999 | Drucker |
| D417,732 S | 12/1999 | Dagsland et al. |
| D417,912 S | 12/1999 | Dagsland et al. |
| 5,996,577 A | 12/1999 | Ohki et al. |
| 5,997,848 A | 12/1999 | Patton et al. |
| 6,001,336 A | 12/1999 | Gordon |
| 6,006,747 A | 12/1999 | Eisele et al. |
| 6,006,753 A | 12/1999 | Efendic |
| D418,600 S | 1/2000 | Haerle |
| D420,736 S | 2/2000 | Moulin |
| 6,026,809 A | 2/2000 | Abrams et al. |
| 6,029,663 A | 2/2000 | Eisele et al. |
| D421,800 S | 3/2000 | Doat |
| 6,039,208 A | 3/2000 | Lambelet et al. |
| 6,043,214 A | 3/2000 | Jensen et al. |
| 6,045,828 A | 4/2000 | Bystorm et al. |
| 6,051,256 A | 4/2000 | Platz et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,063,910 A | 5/2000 | Debenedetti et al. |
| 6,071,497 A | 6/2000 | Steiner et al. |
| 6,073,629 A | 6/2000 | Hardy et al. |
| 6,076,521 A | 6/2000 | Lindahl et al. |
| 6,077,543 A | 6/2000 | Gordon et al. |
| 6,080,762 A | 6/2000 | Allen et al. |
| 6,085,745 A | 6/2000 | Levander et al. |
| D428,486 S | 7/2000 | Schuckmann |
| 6,087,334 A | 7/2000 | Beeley et al. |
| 6,087,351 A | 7/2000 | Nye |
| 6,089,228 A | 7/2000 | Smith et al. |
| 6,095,136 A | 8/2000 | Virtanen |
| 6,098,618 A | 8/2000 | Jennings et al. |
| 6,098,619 A | 8/2000 | Britto et al. |
| 6,102,035 A | 8/2000 | Asking et al. |
| 6,105,571 A | 8/2000 | Coffee |
| 6,105,574 A | 8/2000 | Jahnsson |
| 6,109,261 A | 8/2000 | Clarke et al. |
| 6,109,481 A | 8/2000 | Alexander et al. |
| 6,099,517 A | 9/2000 | Daughtery |
| 6,116,237 A | 9/2000 | Schultz |
| 6,116,238 A | 9/2000 | Jackson et al. |
| 6,116,239 A | 9/2000 | Volgyesi |
| 6,119,684 A | 9/2000 | Nohl et al. |
| 6,119,688 A | 9/2000 | Whaley et al. |
| 6,131,567 A | 10/2000 | Gonda et al. |
| 6,132,766 A | 10/2000 | Sankaram et al. |
| 6,133,235 A | 10/2000 | Galloway et al. |
| 6,142,145 A | 11/2000 | Dagsland |
| 6,152,130 A | 11/2000 | Abrams |
| 6,153,613 A | 11/2000 | Ono et al. |
| 6,155,423 A | 12/2000 | Katzne et al. |
| 6,156,114 A | 12/2000 | Bell et al. |
| 6,158,431 A | 12/2000 | Poole |
| 6,159,360 A | 12/2000 | Gerteis et al. |
| RE37,053 E | 2/2001 | Hanes et al. |
| 6,182,655 B1 | 2/2001 | Keller et al. |
| 6,187,291 B1 | 2/2001 | Weinstein et al. |
| 6,191,102 B1 | 2/2001 | DiMarchi et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| 6,198,847 B1 | 3/2001 | Washizawa |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,250,300 B1 | 6/2001 | Andersson et al. |
| 6,254,854 B1 | 7/2001 | Edwards et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| 6,277,819 B1 | 8/2001 | Efendic |
| 6,279,511 B1 | 8/2001 | Loughnane |
| D448,076 S | 9/2001 | von Shuckmann |
| 6,286,506 B1 | 9/2001 | MacAndrew et al. |
| 6,286,507 B1 | 9/2001 | Jahnsson |
| 6,294,204 B1 | 9/2001 | Rossling et al. |
| D449,684 S | 10/2001 | Christup et al. |
| 6,298,846 B1 | 10/2001 | Ohki et al. |
| 6,298,847 B1 | 10/2001 | Datta et al. |
| D450,117 S | 11/2001 | Braithwaite et al. |
| D451,597 S | 12/2001 | Suh |
| 6,328,034 B1 | 12/2001 | Eisele et al. |
| 6,331,318 B1 | 12/2001 | Milstein |
| D452,910 S | 1/2002 | Braithwaite et al. |
| 6,335,316 B1 | 1/2002 | Hughes et al. |
| D453,264 S | 2/2002 | Acevedo, Jr. |
| 6,347,629 B1 | 2/2002 | Braithwaite |
| 6,348,447 B1 | 2/2002 | Hellstorm et al. |
| 6,357,442 B1 | 3/2002 | Casper et al. |
| 6,358,058 B1 | 3/2002 | Strupat et al. |
| 6,358,924 B1 | 3/2002 | Hoffman |
| 6,360,743 B1 | 3/2002 | Andersson et al. |
| 6,360,929 B1 | 3/2002 | McCarthy |
| D455,208 S | 4/2002 | Bacon et al. |
| 6,363,932 B1 | 4/2002 | Forchione et al. |
| 6,365,190 B1 | 4/2002 | Gordon et al. |
| 6,372,258 B1 | 4/2002 | Platz et al. |
| 6,375,975 B1 | 4/2002 | Modi |
| 6,380,357 B2 | 4/2002 | Hermeling et al. |
| 6,386,195 B1 | 5/2002 | Coffee |
| 6,388,053 B1 | 5/2002 | Galloway et al. |
| 6,394,085 B1 | 5/2002 | Hardy et al. |

(56) References Cited

U.S. PATENT DOCUMENTS

| | | |
|---|---|---|
| 6,395,300 B1 | 5/2002 | Straub et al. |
| 6,395,744 B1 | 5/2002 | Adams et al. |
| 6,395,774 B1 | 5/2002 | Milstein |
| 6,410,513 B1 | 6/2002 | Galloway et al. |
| D460,173 S | 7/2002 | Harrison et al. |
| 6,415,784 B1 | 7/2002 | Christup et al. |
| 6,418,926 B1 | 7/2002 | Chawla |
| 6,423,344 B1 | 7/2002 | Platz et al. |
| D461,239 S | 8/2002 | Cassidy |
| 6,427,688 B1 | 8/2002 | Ligotke et al. |
| 6,428,771 B1 | 8/2002 | Steiner et al. |
| 6,428,805 B1 | 8/2002 | Dohi et al. |
| 6,432,383 B1 | 8/2002 | Modi |
| 6,436,443 B2 | 8/2002 | Edwards et al. |
| 6,439,227 B1 | 8/2002 | Myrman et al. |
| 6,440,463 B1 | 8/2002 | Feldstein et al. |
| 6,441,172 B1 | 8/2002 | Nefzi et al. |
| D463,544 S | 9/2002 | Engelberth et al. |
| 6,443,143 B1 | 9/2002 | Ishida et al. |
| 6,444,226 B1 | 9/2002 | Steiner et al. |
| 6,446,626 B1 | 9/2002 | Virtanen |
| 6,446,627 B1 | 9/2002 | Bowman et al. |
| 6,447,750 B1 | 9/2002 | Cutie et al. |
| 6,447,751 B1 | 9/2002 | Weinstein et al. |
| 6,447,753 B2 | 9/2002 | Edwards et al. |
| 6,451,337 B1 | 9/2002 | Smith et al. |
| 6,457,470 B1 | 10/2002 | Coffee |
| 6,468,507 B1 | 10/2002 | Cutie et al. |
| 6,470,884 B2 | 10/2002 | Horlin |
| 6,479,049 B1 | 11/2002 | Platz et al. |
| 6,484,715 B1 | 11/2002 | Ritsche et al. |
| 6,484,717 B1 | 11/2002 | Dagsland et al. |
| D469,527 S | 1/2003 | Keller et al. |
| 6,503,480 B1 | 1/2003 | Edwards et al. |
| 6,509,006 B1 | 1/2003 | Platz et al. |
| 6,509,313 B1 | 1/2003 | Smith |
| D469,866 S | 2/2003 | Albulet et al. |
| 6,514,482 B1 | 2/2003 | Bartus et al. |
| 6,518,239 B1 | 2/2003 | Kuo et al. |
| 6,523,536 B2 | 2/2003 | Fugelsang et al. |
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,540,982 B1 | 4/2003 | Adjei et al. |
| 6,540,983 B1 | 4/2003 | Adjei et al. |
| 6,543,448 B1 | 4/2003 | Smith et al. |
| 6,546,929 B2 | 4/2003 | Burr et al. |
| 6,555,127 B2 | 4/2003 | Steiner |
| 6,555,521 B2 | 4/2003 | Hermeling et al. |
| D474,536 S | 5/2003 | Albulet et al. |
| D475,133 S | 5/2003 | McLuckie |
| 6,557,549 B2 | 5/2003 | Schmidt et al. |
| 6,561,186 B2 | 5/2003 | Casper et al. |
| 6,567,686 B2 | 5/2003 | Sexton |
| 6,568,390 B2 | 5/2003 | Nichols et al. |
| 6,569,406 B2 | 5/2003 | Stevenson et al. |
| 6,571,793 B1 | 6/2003 | Nilsson et al. |
| 6,572,893 B2 | 6/2003 | Gordon et al. |
| 6,575,160 B1 | 6/2003 | Volgyesi |
| 6,575,162 B1 | 6/2003 | Rand |
| 6,578,571 B1 | 6/2003 | Watt |
| 6,582,728 B1 | 6/2003 | Platz et al. |
| 6,583,111 B1 | 6/2003 | DiMarchi |
| D477,665 S | 7/2003 | Myrman et al. |
| 6,589,560 B2 | 7/2003 | Foster et al. |
| 6,591,832 B1 | 7/2003 | DeJonge |
| 6,592,904 B2 | 7/2003 | Platz et al. |
| 6,595,205 B2 | 7/2003 | Andersson et al. |
| 6,595,208 B1 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,620,910 B1 | 9/2003 | Calas et al. |
| 6,626,173 B2 | 9/2003 | Genova et al. |
| D480,806 S | 10/2003 | Engelberth et al. |
| 6,630,169 B1 | 10/2003 | Bot et al. |
| 6,632,258 B1 | 10/2003 | Wheelock et al. |
| 6,632,456 B1 | 10/2003 | Backstrom et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,644,309 B2 | 11/2003 | Casper et al. |
| 6,645,468 B2 | 11/2003 | Cutie et al. |
| 6,645,504 B1 | 11/2003 | Weiner et al. |
| 6,652,838 B2 | 11/2003 | Weinstein et al. |
| 6,652,885 B2 | 11/2003 | Steiner et al. |
| D483,860 S | 12/2003 | Knoch |
| 6,655,379 B2 | 12/2003 | Clark et al. |
| 6,655,380 B1 | 12/2003 | Andersson et al. |
| 6,655,381 B2 | 12/2003 | Keane et al. |
| 6,660,716 B1 | 12/2003 | Yakubu-Madus et al. |
| 6,663,898 B2 | 12/2003 | Milstein |
| 6,668,826 B1 | 12/2003 | Myrman et al. |
| 6,672,304 B1 | 1/2004 | Casper et al. |
| 6,676,931 B2 | 1/2004 | Dugger, III |
| 6,679,255 B2 | 1/2004 | Pera |
| 6,681,767 B1 | 1/2004 | Patton et al. |
| 6,681,768 B2 | 1/2004 | Haaije de Boer et al. |
| 6,685,967 B1 | 2/2004 | Patton et al. |
| 6,698,421 B2 | 3/2004 | Attolini |
| 6,698,422 B2 | 3/2004 | Fugelsang et al. |
| 6,701,917 B2 | 3/2004 | O'Leary |
| 6,703,361 B2 | 3/2004 | Weiner et al. |
| 6,703,365 B2 | 3/2004 | Galloway et al. |
| 6,703,381 B1 | 3/2004 | Ekwuribe et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B1 | 4/2004 | Hughes et al. |
| 6,722,363 B1 | 4/2004 | von Schuckmann |
| D489,448 S | 5/2004 | Shayan |
| 6,729,324 B2 | 5/2004 | Casper et al. |
| 6,729,328 B2 | 5/2004 | Raul |
| 6,737,045 B2 | 5/2004 | Patton |
| 6,745,761 B2 | 6/2004 | Christup et al. |
| 6,747,006 B2 | 6/2004 | Efendic |
| 6,748,946 B1 | 6/2004 | Rand et al. |
| 6,748,947 B2 | 6/2004 | Keane et al. |
| 6,752,145 B1 | 6/2004 | Bonney et al. |
| 6,755,190 B2 | 6/2004 | Rasmussen |
| D492,769 S | 7/2004 | Hatanaka |
| D493,220 S | 7/2004 | Burge et al. |
| D493,519 S | 7/2004 | Jonsson et al. |
| 6,774,112 B2 | 8/2004 | Gougoutas |
| 6,787,152 B2 | 9/2004 | Kirby et al. |
| 6,790,496 B1 | 9/2004 | Levander et al. |
| 6,792,945 B2 | 9/2004 | Davies et al. |
| 6,797,258 B2 | 9/2004 | Platz et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,821,949 B2 | 11/2004 | Bridon et al. |
| 6,823,863 B2 | 11/2004 | Huxham et al. |
| D499,802 S | 12/2004 | Pinon et al. |
| 6,830,046 B2 | 12/2004 | Blakley et al. |
| 6,838,075 B2 | 1/2005 | Stevenson et al. |
| 6,838,076 B2 | 1/2005 | Platton et al. |
| 6,847,595 B2 | 1/2005 | Tanaka |
| 6,848,443 B2 | 2/2005 | Schmidt et al. |
| 6,849,708 B1 | 2/2005 | Habener |
| 6,852,690 B1 | 2/2005 | Nauck et al. |
| 6,858,199 B1 | 2/2005 | Edwards et al. |
| 6,860,262 B2 | 3/2005 | Christup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |

(56) References Cited

U.S. PATENT DOCUMENTS

| | | |
|---|---|---|
| 6,881,423 B2 | 4/2005 | Dohi et al. |
| 6,884,435 B1 | 4/2005 | O'Hagan et al. |
| 6,887,459 B1 | 5/2005 | Haeberlin |
| 6,887,849 B2 | 5/2005 | Bridon et al. |
| 6,889,687 B1 | 5/2005 | Olsson |
| 6,892,728 B2 | 5/2005 | Helgesson et al. |
| 6,896,906 B2 | 5/2005 | Hastedt et al. |
| D506,680 S | 6/2005 | Saelzer |
| 6,904,907 B2 | 6/2005 | Speldrich et al. |
| 6,906,030 B2 | 6/2005 | Milstein |
| 6,916,354 B2 | 7/2005 | Elliot |
| 6,918,991 B2 | 7/2005 | Chickering, III et al. |
| 6,921,458 B2 | 7/2005 | Chickering, III et al. |
| 6,921,528 B2 | 7/2005 | Edwards et al. |
| 6,923,175 B2 | 8/2005 | Poole et al. |
| D509,296 S | 9/2005 | Minshull et al. |
| D509,898 S | 9/2005 | Bunce et al. |
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Joregenson et al. |
| D511,208 S | 11/2005 | Pardonge et al. |
| D511,977 S | 11/2005 | Saelzer |
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| 6,989,155 B1 | 1/2006 | Ganderton et al. |
| 6,991,779 B2 | 1/2006 | Steiner et al. |
| D515,696 S | 2/2006 | Lucking et al. |
| D515,924 S | 2/2006 | Grant |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,107,988 B2 | 9/2006 | Pinon et al. |
| D529,604 S | 10/2006 | Young et al. |
| 7,125,566 B2 | 10/2006 | Etter |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 | 12/2006 | Godfrey |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| 7,185,650 B2 | 3/2007 | Huber et al. |
| D538,423 S | 3/2007 | Berube et al. |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Hammer et al. |
| D548,330 S | 8/2007 | Cox et al. |
| D548,618 S | 8/2007 | Ferguson et al. |
| D548,619 S | 8/2007 | Ferguson et al. |
| D548,833 S | 8/2007 | Young et al. |
| D549,111 S | 8/2007 | Ferguson et al. |
| 7,258,118 B2 | 8/2007 | Goede et al. |
| 7,259,233 B2 | 8/2007 | Dodd et al. |
| D550,835 S | 9/2007 | Tanaka et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Mryman et al. |
| 7,278,843 B2 | 10/2007 | Feldstein et al. |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,512,069 B2 | 4/2009 | Patton et al. |
| 7,517,874 B2 | 4/2009 | Beckett et al. |
| 7,520,278 B2 | 4/2009 | Crowder et al. |
| 7,533,668 B1 | 5/2009 | Widerstrom |
| D594,753 S | 6/2009 | Eadicicco et al. |
| 7,556,798 B2 | 7/2009 | Edwards et al. |
| 7,559,322 B2 | 7/2009 | Foley et al. |
| D597,418 S | 8/2009 | Stojek |
| D597,657 S | 8/2009 | Kinsey et al. |
| D598,785 S | 8/2009 | Stojek |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo |
| 7,648,960 B2 | 1/2010 | Steiner et al. |
| D613,849 S | 4/2010 | Smutney |

(56) References Cited

U.S. PATENT DOCUMENTS

| | | |
|---|---|---|
| D614,045 S | 4/2010 | Gaudenzi et al. |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| D620,812 S | 8/2010 | Gaudenzi et al. |
| 7,794,754 B2 | 9/2010 | Feldstein et al. |
| 7,799,344 B2 | 9/2010 | Oberg |
| 7,803,404 B2 | 9/2010 | Hokenson |
| 7,820,676 B2 | 10/2010 | Leone-Bay et al. |
| D628,090 S | 11/2010 | Stuiber et al. |
| 7,833,549 B2 | 11/2010 | Steiner et al. |
| 7,833,550 B2 | 11/2010 | Steiner et al. |
| 7,842,662 B2 | 11/2010 | Schteingart et al. |
| D629,505 S | 12/2010 | Adamo |
| D629,506 S | 12/2010 | Adamo |
| D629,886 S | 12/2010 | Adamo |
| D629,887 S | 12/2010 | Adamo |
| D629,888 S | 12/2010 | Adamo |
| D635,241 S | 3/2011 | McLean |
| D635,242 S | 3/2011 | Adamo |
| D635,243 S | 3/2011 | Kinsey |
| 7,913,688 B2 | 3/2011 | Cross |
| D636,867 S | 4/2011 | Polidoro et al. |
| D636,868 S | 4/2011 | Kinsey et al. |
| D636,869 S | 4/2011 | Laurenzi et al. |
| 7,919,119 B2 | 4/2011 | Straub et al. |
| 7,943,178 B2 | 5/2011 | Steiner et al. |
| 7,943,572 B2 | 5/2011 | Cheatham et al. |
| 7,954,491 B2 | 6/2011 | Hrkach |
| 7,959,609 B2 | 6/2011 | Gaydos et al. |
| D641,076 S | 7/2011 | Grunstad et al. |
| D643,308 S | 8/2011 | Bergey |
| D645,954 S | 9/2011 | Hately |
| D647,195 S | 10/2011 | Clarke et al. |
| D647,196 S | 10/2011 | Clarke et al. |
| 8,037,880 B2 | 10/2011 | Zhu et al. |
| 8,037,881 B2 | 10/2011 | Pentafragas |
| 8,039,431 B2 | 10/2011 | Wilson et al. |
| 8,047,203 B2 | 11/2011 | Young et al. |
| D652,322 S | 1/2012 | Stuiber et al. |
| 8,109,267 B2 | 2/2012 | Villax et al. |
| 8,119,593 B2 | 2/2012 | Richardson |
| D655,622 S | 3/2012 | Sadler et al. |
| 8,133,514 B2 | 3/2012 | Milstein |
| 8,146,588 B2 | 4/2012 | Steiner et al. |
| 8,156,936 B2 | 4/2012 | Steiner et al. |
| D659,020 S | 5/2012 | Kemner |
| D659,022 S | 5/2012 | Kemner |
| 8,166,970 B2 | 5/2012 | Poole et al. |
| 8,172,817 B2 | 5/2012 | Michaels et al. |
| 8,196,576 B2 | 6/2012 | Kriksunov et al. |
| 8,201,555 B2 | 6/2012 | Chawla |
| 8,202,992 B2 | 6/2012 | Stevenson |
| D664,640 S | 7/2012 | Smutney et al. |
| 8,215,300 B2 | 7/2012 | Steiner et al. |
| 8,217,007 B1 | 7/2012 | Schteingart et al. |
| 8,227,409 B2 | 7/2012 | Kraft |
| 8,236,766 B2 | 8/2012 | Schteingart et al. |
| 8,252,916 B2 | 8/2012 | Simard et al. |
| 8,258,095 B2 | 9/2012 | Boss et al. |
| 8,278,308 B2 | 10/2012 | Leone-Bay et al. |
| 8,293,869 B2 | 10/2012 | Bossard |
| 8,314,106 B2 | 11/2012 | Kraft |
| D671,842 S | 12/2012 | Bergey |
| D674,893 S | 1/2013 | Kinsey et al. |
| 8,372,804 B2 | 2/2013 | Richardson |
| 8,377,869 B2 | 2/2013 | Richardson |
| 8,389,470 B2 | 3/2013 | Steiner |
| 8,394,414 B2 | 3/2013 | Steiner et al. |
| 8,408,200 B2 | 4/2013 | Clark et al. |
| 8,420,604 B2 | 4/2013 | Hokenson |
| 8,424,518 B2 | 4/2013 | Smutney |
| 8,485,180 B2 | 7/2013 | Smutney et al. |
| 8,486,894 B2 | 7/2013 | Schteingart et al. |
| 8,499,757 B2 | 8/2013 | Smutney |
| 8,512,932 B2 | 8/2013 | Wilson et al. |
| 8,522,775 B2 | 9/2013 | Malhotra et al. |
| 8,536,131 B2 | 9/2013 | Schteingart et al. |
| 8,538,707 B2 | 9/2013 | Adamo et al. |
| 8,539,946 B2 | 9/2013 | Esteve et al. |
| 8,551,528 B2 | 10/2013 | Grant et al. |
| 8,563,101 B2 | 10/2013 | Spallek |
| 8,636,001 B2 | 1/2014 | Smutney |
| 8,642,548 B2 | 2/2014 | Richardson et al. |
| 8,671,937 B2 | 3/2014 | Steiner et al. |
| 8,677,992 B2 | 3/2014 | Villax |
| 8,763,606 B2 | 7/2014 | Mosier et al. |
| 8,778,403 B2 | 7/2014 | Grant et al. |
| 8,783,249 B2 | 7/2014 | Poole et al. |
| 8,808,786 B2 | 8/2014 | Jinks et al. |
| 8,820,324 B2 | 9/2014 | Smith et al. |
| 8,909,487 B2 | 12/2014 | Adamo et al. |
| 8,925,726 B2 | 1/2015 | Bergey |
| 9,041,925 B2 | 5/2015 | Adamo et al. |
| 9,138,407 B2 | 9/2015 | Caponetti et al. |
| 2001/0020147 A1 | 9/2001 | Staniforth et al. |
| 2001/0039442 A1 | 11/2001 | Gorge et al. |
| 2002/0000225 A1 | 1/2002 | Schuler et al. |
| 2002/0033177 A1 | 3/2002 | Ohki et al. |
| 2002/0052381 A1 | 5/2002 | Bar-Or et al. |
| 2002/0053344 A1 | 5/2002 | Davies et al. |
| 2002/0053347 A1 | 5/2002 | Ziaee |
| 2002/0065239 A1 | 5/2002 | Caplan et al. |
| 2002/0088462 A1 | 7/2002 | Genova et al. |
| 2002/0101590 A1 | 8/2002 | Shimaoka |
| 2002/0144680 A1 | 10/2002 | Nilsson et al. |
| 2002/0161001 A1 | 10/2002 | Kanstrup et al. |
| 2003/0000524 A1 | 1/2003 | Andersson et al. |
| 2003/0010794 A1 | 1/2003 | Herdtle et al. |
| 2003/0013641 A1 | 1/2003 | Steiner et al. |
| 2003/0017211 A1 | 1/2003 | Steiner |
| 2003/0053960 A1 | 3/2003 | Heijerman et al. |
| 2003/0064097 A1 | 4/2003 | Patel et al. |
| 2003/0068378 A1 | 4/2003 | Chen et al. |
| 2003/0099636 A1 | 5/2003 | Epshtein et al. |
| 2003/0136405 A1 | 7/2003 | Goede et al. |
| 2003/0194420 A1 | 10/2003 | Holl et al. |
| 2003/0235538 A1 | 12/2003 | Zirenberg |
| 2004/0024180 A1 | 2/2004 | Drauz |
| 2004/0025875 A1 | 2/2004 | Reber et al. |
| 2004/0034014 A1 | 2/2004 | Kanstrup et al. |
| 2004/0038865 A1 | 2/2004 | Gelber et al. |
| 2004/0053819 A1 | 3/2004 | Dodd et al. |
| 2004/0062722 A1 | 4/2004 | Gonda et al. |
| 2004/0076588 A1 | 4/2004 | Batycky et al. |
| 2004/0077528 A1 | 4/2004 | Steiner et al. |
| 2004/0096403 A1 | 5/2004 | Steiner |
| 2004/0107963 A1 | 6/2004 | Finlay et al. |
| 2004/0121964 A1 | 6/2004 | Madar et al. |
| 2004/0138099 A1 | 7/2004 | Draeger |
| 2004/0151059 A1 | 8/2004 | Robert, II et al. |
| 2004/0151774 A1 | 8/2004 | Pauletti et al. |
| 2004/0157928 A1 | 8/2004 | Kim et al. |
| 2004/0163648 A1 | 8/2004 | Burton |
| 2004/0182387 A1 | 9/2004 | Steiner et al. |
| 2004/0187869 A1 | 9/2004 | Bjorndal et al. |
| 2004/0204439 A1 | 10/2004 | Staniforth et al. |
| 2004/0204440 A1 | 10/2004 | Staniforth et al. |
| 2004/0211419 A1 | 10/2004 | Eason et al. |
| 2004/0234615 A1 | 11/2004 | Sabetsky |
| 2004/0234616 A1 | 11/2004 | Sabetsky |
| 2004/0241232 A1 | 12/2004 | Brown et al. |
| 2004/0247628 A1 | 12/2004 | Lintz et al. |
| 2004/0250812 A1 | 12/2004 | Davies et al. |
| 2005/0000518 A1 | 1/2005 | Dunkley et al. |
| 2005/0039743 A1 | 2/2005 | Taylor |
| 2005/0043228 A1 | 2/2005 | DeFelippis et al. |
| 2005/0043247 A1 | 2/2005 | Trunk et al. |
| 2005/0056281 A1 | 3/2005 | Snow |
| 2005/0070469 A1 | 3/2005 | Bloom |

(56) References Cited

U.S. PATENT DOCUMENTS

| | | |
|---|---|---|
| 2005/0080000 A1 | 4/2005 | Thurow et al. |
| 2005/0119604 A1 | 6/2005 | Bonney et al. |
| 2005/0124644 A1 | 6/2005 | Nilsson et al. |
| 2005/0147581 A1 | 7/2005 | Zamiri et al. |
| 2005/0153874 A1 | 7/2005 | Cheatham et al. |
| 2005/0155601 A1 | 7/2005 | Steiner et al. |
| 2005/0183723 A1 | 8/2005 | Pinon et al. |
| 2005/0187749 A1 | 8/2005 | Singley |
| 2005/0214251 A1 | 9/2005 | Pohl et al. |
| 2005/0252508 A1 | 11/2005 | Koerner |
| 2005/0265927 A1 | 12/2005 | Lee |
| 2005/0274378 A1 | 12/2005 | Bonney et al. |
| 2006/0000469 A1 | 1/2006 | Tseng |
| 2006/0003316 A1 | 1/2006 | Simard et al. |
| 2006/0040953 A1 | 2/2006 | Leone-Bay et al. |
| 2006/0041133 A1 | 2/2006 | Stevenson et al. |
| 2006/0099269 A1 | 5/2006 | Cheatham et al. |
| 2006/0120969 A1 | 6/2006 | Nilsson et al. |
| 2006/0153778 A1 | 7/2006 | Gelber et al. |
| 2006/0160722 A1 | 7/2006 | Green et al. |
| 2006/0165756 A1 | 7/2006 | Catani et al. |
| 2006/0239933 A1 | 10/2006 | Nilsson et al. |
| 2006/0239934 A1 | 10/2006 | Cheatham et al. |
| 2006/0243275 A1 | 11/2006 | Ruckdeschel et al. |
| 2006/0249419 A1 | 11/2006 | Taylor et al. |
| 2006/0260777 A1 | 11/2006 | Rashba-Step et al. |
| 2006/0283758 A1 | 12/2006 | Pasbrig |
| 2007/0006876 A1 | 1/2007 | Finlay et al. |
| 2007/0017506 A1 | 1/2007 | Bell et al. |
| 2007/0020191 A1 | 1/2007 | Boss et al. |
| 2007/0027063 A1 | 2/2007 | Boss et al. |
| 2007/0044793 A1 | 3/2007 | Kleinstreuer et al. |
| 2007/0049576 A1 | 3/2007 | Barlow et al. |
| 2007/0059373 A1 | 3/2007 | Oberg |
| 2007/0059374 A1 | 3/2007 | Hokenson et al. |
| 2007/0074989 A1 | 4/2007 | Merboth et al. |
| 2007/0077219 A1 | 4/2007 | Fahl et al. |
| 2007/0086952 A1 | 4/2007 | Steiner |
| 2007/0099454 A1 | 5/2007 | Gordon |
| 2007/0125375 A1 | 6/2007 | Finlay et al. |
| 2007/0128193 A1 | 6/2007 | O'Neil et al. |
| 2007/0151562 A1 | 7/2007 | Jones |
| 2007/0191462 A1 | 8/2007 | Hettiarachchi |
| 2007/0196503 A1 | 8/2007 | Wilson et al. |
| 2007/0207958 A1 | 9/2007 | Bridon et al. |
| 2007/0225587 A1 | 9/2007 | Burnell et al. |
| 2007/0235029 A1 | 10/2007 | Zhu et al. |
| 2007/0240708 A1 | 10/2007 | Schuckmann |
| 2007/0272763 A1 | 11/2007 | Dunne et al. |
| 2007/0277820 A1 | 12/2007 | Crowder et al. |
| 2007/0277821 A1 | 12/2007 | Oliva et al. |
| 2007/0295332 A1 | 12/2007 | Ziegler |
| 2007/0299074 A1 | 12/2007 | Netz et al. |
| 2008/0008764 A1 | 1/2008 | Milstein |
| 2008/0015457 A1 | 1/2008 | Silva |
| 2008/0047550 A2 | 2/2008 | Steiner et al. |
| 2008/0066739 A1 | 3/2008 | LeMahieu et al. |
| 2008/0108554 A1 | 5/2008 | Jackson et al. |
| 2008/0108574 A1 | 5/2008 | Barlow et al. |
| 2008/0115785 A1 | 5/2008 | Eason et al. |
| 2008/0127970 A1 | 6/2008 | Steiner et al. |
| 2008/0127974 A1 | 6/2008 | Lastow |
| 2008/0129791 A1 | 6/2008 | King et al. |
| 2008/0168987 A1 | 7/2008 | Denny et al. |
| 2008/0190424 A1 | 8/2008 | Lucking et al. |
| 2008/0197044 A1 | 8/2008 | Hickey et al. |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2008/0295833 A1 | 12/2008 | Rohrschneider et al. |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0134051 A1 | 5/2009 | Rapp et al. |
| 2009/0149727 A1 | 6/2009 | Truitt et al. |
| 2009/0151720 A1 | 6/2009 | Inoue et al. |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0314292 A1 | 12/2009 | Overfield |
| 2009/0320837 A1 | 12/2009 | Smith et al. |
| 2010/0012120 A1 | 1/2010 | Herder |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0212667 A1 | 8/2010 | Smith et al. |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0288276 A1 | 11/2010 | Ganderton et al. |
| 2010/0326438 A1 | 12/2010 | Dunne |
| 2011/0000482 A1 | 1/2011 | Gumaste et al. |
| 2011/0003004 A1 | 1/2011 | Hokenson |
| 2011/0011394 A1 | 1/2011 | Edwards et al. |
| 2011/0083667 A1 | 4/2011 | Briant |
| 2011/0158935 A1 | 6/2011 | Kraft |
| 2011/0183901 A1 | 7/2011 | Cheatham |
| 2012/0014999 A1 | 1/2012 | Grant et al. |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adamo et al. |
| 2012/0247465 A1 | 10/2012 | Wachtel |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0118491 A1 | 5/2013 | Richardson et al. |
| 2013/0125886 A1 | 5/2013 | Richardson et al. |
| 2013/0143801 A1 | 6/2013 | Steiner et al. |
| 2013/0189365 A1 | 7/2013 | Hokenson |
| 2013/0199527 A1 | 8/2013 | Smutney et al. |
| 2013/0289278 A1 | 10/2013 | Kraft |
| 2013/0291866 A1 | 11/2013 | Smutney |
| 2013/0291867 A1 | 11/2013 | Smutney |
| 2013/0303445 A1 | 11/2013 | Wilson et al. |
| 2013/0338065 A1 | 12/2013 | Smutney |
| 2014/0007873 A1 | 1/2014 | Smutney |
| 2014/0014106 A1 | 1/2014 | Smutney |
| 2014/0083421 A1 | 3/2014 | Smutney |
| 2014/0096771 A1 | 4/2014 | Remmelgas et al. |
| 2014/0100158 A1 | 4/2014 | Richardson et al. |
| 2014/0187490 A1 | 7/2014 | Richardson et al. |
| 2014/0199398 A1 | 7/2014 | Grant et al. |
| 2014/0227359 A1 | 8/2014 | Leone-Bay et al. |
| 2014/0243530 A1 | 8/2014 | Stevenson et al. |
| 2014/0271888 A1 | 9/2014 | Grant et al. |
| 2014/0290654 A1 | 10/2014 | Poole et al. |
| 2014/0302151 A1 | 10/2014 | Leone-Bay et al. |
| 2014/0308358 A1 | 10/2014 | Oberg et al. |
| 2014/0315953 A1 | 10/2014 | Leone-Bay et al. |
| 2015/0031609 A1 | 1/2015 | Steiner et al. |

(56) References Cited

U.S. PATENT DOCUMENTS

| | | |
|---|---|---|
| 2015/0045295 A1 | 2/2015 | Smutney et al. |
| 2015/0052977 A1 | 2/2015 | Adamo et al. |
| 2015/0065422 A1 | 3/2015 | Kraft |
| 2015/0080298 A1 | 3/2015 | Costello et al. |
| 2015/0108023 A1 | 4/2015 | Bergey |
| 2015/0122258 A1 | 5/2015 | Steiner et al. |
| 2015/0150980 A1 | 6/2015 | Leone-Bay et al. |
| 2015/0174210 A1 | 6/2015 | Boss et al. |
| 2015/0196724 A1 | 7/2015 | Adamo et al. |
| 2015/0226656 A1 | 8/2015 | Adamo et al. |
| 2015/0231067 A1 | 8/2015 | Mann |
| 2015/0246188 A1 | 9/2015 | Steiner et al. |
| 2015/0283213 A1 | 10/2015 | Costello et al. |
| 2015/0290132 A1 | 10/2015 | Gelber et al. |

FOREIGN PATENT DOCUMENTS

| | | |
|---|---|---|
| CN | 101851213 | 10/2010 |
| DE | 2840442 C2 | 2/1982 |
| DE | 3639836 A1 | 6/1988 |
| DE | 19519840 A1 | 12/1996 |
| EP | 69715 | 1/1983 |
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 387222 A | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 640354 B1 | 12/2001 |
| EP | 1364967 | 11/2003 |
| EP | 825885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A1 | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2398065 A | 8/2004 |
| JP | 63-020301 | 1/1988 |
| JP | 2115154 A | 4/1990 |
| JP | 2-149545 | 2/1992 |
| JP | H07-041428 | 2/1995 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| JP | 2007-061281 | 3/2007 |
| TW | 200505517 A | 2/2005 |
| WO | 1990/013285 | 11/1990 |
| WO | 1991/004011 | 4/1991 |
| WO | 1991/006287 | 5/1991 |
| WO | 1991/016038 | 10/1991 |
| WO | 1991/016882 | 11/1991 |
| WO | 1991/019524 | 12/1991 |
| WO | 1992/004069 | 3/1992 |
| WO | 1992/008509 | 5/1992 |
| WO | 1993/002712 | 2/1993 |
| WO | 1993/014110 | 7/1993 |
| WO | 1993/017728 | 9/1993 |
| WO | 1993/018754 A1 | 9/1993 |
| WO | 1994/000291 | 1/1994 |
| WO | 1994/008552 | 4/1994 |
| WO | 1994/008599 | 4/1994 |
| WO | 1994/019041 | 9/1994 |
| WO | 1994/023702 | 10/1994 |
| WO | 1994/025005 A1 | 11/1994 |
| WO | 1995/000127 A1 | 1/1995 |
| WO | 1995/005208 | 2/1995 |
| WO | 1995/011666 | 5/1995 |
| WO | 1995/024183 A1 | 9/1995 |
| WO | 1995/031979 | 11/1995 |
| WO | 1995/034294 | 12/1995 |
| WO | 1996/001105 | 1/1996 |
| WO | 1996/005810 | 2/1996 |
| WO | 1996/013250 | 5/1996 |
| WO | 1996/022802 A | 8/1996 |
| WO | 1996/027386 A1 | 9/1996 |
| WO | 1996/032149 | 10/1996 |
| WO | 1996/036314 | 11/1996 |
| WO | 1996/036317 A1 | 11/1996 |
| WO | 1996/040206 A1 | 12/1996 |
| WO | 1997/001365 | 1/1997 |
| WO | 1997/004747 | 2/1997 |
| WO | 1997/025086 A2 | 7/1997 |
| WO | 1997/030743 | 8/1997 |
| WO | 1997/035562 A1 | 10/1997 |
| WO | 1997/046206 | 12/1997 |
| WO | 1997/049386 | 12/1997 |
| WO | 1998/026827 A1 | 6/1998 |
| WO | 1998/039043 | 9/1998 |
| WO | 1998/041255 A2 | 9/1998 |
| WO | 1998/043615 | 10/1998 |
| WO | 1999/014239 A1 | 3/1999 |
| WO | 1999/018939 A1 | 4/1999 |
| WO | 1999/032510 A1 | 7/1999 |
| WO | 1999/033862 | 7/1999 |
| WO | 1999/052506 | 10/1999 |
| WO | 2000/12116 | 3/2000 |
| WO | 2000/033811 A2 | 6/2000 |
| WO | 2000/059476 A1 | 10/2000 |
| WO | 2000/071154 A2 | 11/2000 |
| WO | 2001/000654 | 1/2001 |
| WO | 2001/081321 A | 1/2001 |
| WO | 2001/049274 A2 | 7/2001 |
| WO | 2001/051071 | 7/2001 |
| WO | 2001/052813 A1 | 7/2001 |
| WO | 2001/066064 | 9/2001 |
| WO | 2001/068169 | 9/2001 |
| WO | 2001/097886 A1 | 12/2001 |
| WO | 2001/007107 | 2/2002 |
| WO | 2002/011676 | 2/2002 |
| WO | 2002/012201 A1 | 2/2002 |
| WO | 2002/047659 A2 | 6/2002 |
| WO | 2002/058735 | 8/2002 |
| WO | 2002/059574 A1 | 8/2002 |
| WO | 2002/067995 A1 | 9/2002 |
| WO | 2002/085281 | 10/2002 |
| WO | 2002/098348 | 12/2002 |
| WO | 2002/102444 | 12/2002 |
| WO | 2003/000202 | 1/2003 |
| WO | 2003/022304 A1 | 3/2003 |
| WO | 2003/055547 A1 | 7/2003 |
| WO | 2003/057170 | 7/2003 |
| WO | 2003/061578 A2 | 7/2003 |
| WO | 2003/072195 A2 | 9/2003 |
| WO | 2003/080149 A2 | 10/2003 |
| WO | 2003/086345 | 10/2003 |
| WO | 2003/094951 | 11/2003 |
| WO | 2004/012672 | 2/2004 |
| WO | 2004/012720 | 2/2004 |
| WO | 2004/033010 | 4/2004 |

(56) References Cited

FOREIGN PATENT DOCUMENTS

| | | |
|---|---|---|
| WO | 2004/035121 | 4/2004 |
| WO | 2004/041338 | 5/2004 |
| WO | 2004/050152 | 6/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |
| WO | 2005/020964 | 3/2005 |
| WO | 2005/023348 A | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/016600 A2 | 2/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/033372 A2 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060484 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/047921 A1 | 4/2009 |
| WO | 2009/055030 | 4/2009 |
| WO | 2009/055740 | 4/2009 |
| WO | 2009/055742 | 4/2009 |
| WO | 2009/095684 A1 | 8/2009 |
| WO | 2009/121020 A1 | 10/2009 |
| WO | 2009/140587 A1 | 11/2009 |
| WO | 2009/152477 A2 | 12/2009 |
| WO | 2009/155581 A1 | 12/2009 |
| WO | 2010/021879 A2 | 2/2010 |
| WO | 2010/078373 A1 | 7/2010 |
| WO | 2010/080964 | 7/2010 |
| WO | 2010/102148 | 9/2010 |
| WO | 2010/105094 A1 | 9/2010 |
| WO | 2010/108046 A1 | 9/2010 |
| WO | 2010/125103 A1 | 11/2010 |
| WO | 2010/144785 A2 | 12/2010 |
| WO | 2010/144789 | 12/2010 |
| WO | WO2010144789 * | 12/2010 |
| WO | 2011/017554 A2 | 2/2011 |
| WO | 2011/056889 A1 | 5/2011 |
| WO | 2011/163272 | 12/2011 |
| WO | 2012/064892 A1 | 5/2012 |
| WO | 2012/135765 | 10/2012 |
| WO | 2012/174472 A1 | 12/2012 |
| WO | 2012/174556 A1 | 12/2012 |
| WO | 2013/063160 A1 | 5/2013 |
| WO | 2014/012069 A2 | 1/2014 |
| WO | 2014/036323 A1 | 3/2014 |
| WO | 2014/066856 A1 | 5/2014 |
| WO | 2014/0144895 A1 | 9/2014 |
| WO | 2015/010092 A1 | 1/2015 |
| WO | 2015/021064 A1 | 2/2015 |
| WO | 2015/148905 A1 | 10/2015 |

OTHER PUBLICATIONS

Amodeo et al., Pain peptides. Solution structure of orphanin FQ2. FEBS Letters, vol. 473, Issue 2, pp. 157-160 (2000).

Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).

Amorij et al., Development of stable infleunza vaccine powder formulations challenges and possibilities. Pharmaceutical Research, vol. 25, No. 6, pp. 1256-1273 (2008).

Audouy et al., Development of a dried influenza whole inactivated virus vaccine for pulmonary immunization. Vaccine, vol. 29, pp. 4345-4352 (2011).

Volund "Conversion of insulin units to SI units." American Journal of Clinical Nutrition, Nov. 1993, 58(5), pp. 714-715.

Wachters-Hagedoorn et al. "The rate of intestinal glucose absorption is correlated with plasma glucose-dependent insulinotropic polypeptide concentrations in healthy men." J Nutr 136:1511, 2006.

Wang et al., Glucagon-like peptide-1 is a physiological incretin in rat. J. Clin. Invest., 95 : 417-421 (1995).

Wang et al., Glucagon-like peptide-1 regulates proliferation and apoptosis via activation of protein kinase B in pancreatic INS-1 beta cells. Diabetologia, 47:478-487, 2004.

Wareham et al., "Fasting Proinsulin Concentrations Predict the Development of Type 2 Diabetes", Diabetes Care, 1999, 22, 262-70.

Warren et al. "Postprandial versus prandial dosing of biphasic insulin aspart in elderly type 2 diabetes patients." Diabetes Res Clin Pract 66:23-29, 2004.

Waterhouse et al., "Comparatie assessment of a new breath-actuated inhaler in patients with reversible airways obstruction", Respiration 59:155-158 (1992).

WebMD (retrieved from http://www.webmd.com/pain-management/tc/pain-management-side-effects-of-pain-medicines in 2012, 4 pages).

Wei et al. "Tissue-specific expression of the human receptor for glucagon-like peptide-1: brain and pancreatic forms have the same deduced amino acid sequence." FEBS Letters 358:219, 1995.

Weir et al. "Glucagonlike peptide 1 (7-37) actions on endocrine pancreas." Diabetes 38:338, 1989.

Weiss, SR et al. "Inhaled insulin provides improved glycemic control in patients with type 2 diabetes mellitus inadequately controlled with oral agents." Arch Intern Med 163:2277-2282, 2003.

Weissberger, "Mannkind: Overlooked Biotech with Excellent Prospects (Part V)," http://www.investorvillage.com/smbd.asp?mb=2885&mn=45817&pt=msg&mid=5021385 (posted on Jun. 19, 2008, accessed on Oct. 18, 2012).

West, Solid State Chemistry and its Applications, Chp 10, Solid Solutions. Wiley, New York, 358 (1998).

(56) References Cited

OTHER PUBLICATIONS

Wettergren A et al. "Truncated GLP-1 (proglucagon 78-107-Amide) inhibits gastric and pancreatic functions in man." Digestive Diseases and Sciences 38:665, 1993.
White Jr et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11): 4542-4546 (2007).
Yoshida et al., Absorption of insulin delivered to rabbit trachea using aerosol dosage form. J. Pharm. Sci. 68(5): 670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
Bosquillon et al., Pulmonary delivery of growth hormone using dry powders and visualization of its local fate in rates. Journal of Controlled Release 96: 233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, cited in Office Action dated Mar. 26, 2015 in U.S. Appl. No. 13/942,482.
Definition of matrix from http://medical-dictionary.thefreedictionary.com/matrix, cited in Office Action dated Mar. 26, 2015 in U.S. Appl. No. 12/471,260.
Diabetes Frontier, vol. 10, No. 5, p. 647-657 (1999) (full Japanese article with translated English portion provided in separate attachment, portion translated in English is the bottom of p. 655 and the left column of p. 656).
Ely et al., Effervescent dry powder for respiratory drug delivery. European Journal of Pharmaceutics and Biopharmaceutics 65: 346-353 (2007).
European Search report for European Application 14192154.4 dated Mar. 19, 2015.
Extended European Search report for European Application 14187552.6 dated Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation dosage forms of insulin with spray fluidized bed granulating system. J. Soc. Powder Technol., Japan, 41: 514-521 (2004).
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).

(56) References Cited

OTHER PUBLICATIONS

Oberdorster et al.,Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 64, pp. 373-379 (2007).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009 , Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration luring administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, pp. 235-247.
Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, pp. 2276-2281.
Pesic, Inhaler delivers more drug to the deep lung, says Cambridge Consultants. in-Pharma Technologist.com, http://www//in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Oterbach K. Effect of Technosphere® inhaled insulin ontreatment satisfaction, glycemic control and quality of life. Diabetes 2006; 55:Abstract 423-P.
Pezron et al., Insulin aggregation and asymmetric transport across human bronchial epthelial cell monolayers (Calu-3). J. Pharmaceutical Sci. 91: 1135-1146 (2002).

Pfeiffer MA et al. Insulin secretion in diabetes mellitus. Am J Med 70:579-88, 1981.
Pfutzner et al., Abstract 812; Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technospher(TM) drug carrier mechanism." Expert Opin Drug Deliv 2:1097-1106, 2005.
Pfützner A et al. "Technosphere®/Insulin—a new approach for the effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Shields, Irritable bowel syndrome, archived Jun. 21, 2009, available at: https://web.archive.org/web/200906211 00502/http://www.gastroenterologistpaloalto.com/conditions-diseases-irritable-bowelsyndrome-palo-alto-ca. html;Aug. 26, 2015 is U.S. Appl. No. 14/139,714.
Smith et al., Evaluation of novel aerosol formulations designed for mucosal vaccination against infleunza virus. Vacine, vol. 21, pp. 2805-2812 (2003).
U.S. Appl. No. 14/873,041, filed Oct. 1, 2015.
U.S. Appl. No. 29/504,212, filed Oct. 2, 2014.
U.S. Appl. No. 14/774,311, filed Sep. 10, 2015.
U.S. Appl. No. 14/746,656, filed Jun. 22, 2015.
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust: Definitions and Concepts [retrieved from internet by Examiner in European case on Sep. 22, 2015]. <URL: http://www.who.int/occupational_health/publications/airdust/en/> published on Oct. 29, 2004 as per Wayback Machine.
Owens et al., Blood glucose self-monitoring in type 1 and type 2 diabetes: reaching a multidisciplinary consensus. Diabetes and Primary Care, vol. 6, No. 1, pp. 8-16 (2004).
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. (Original and English translation provided in one document).
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.

(56) References Cited

OTHER PUBLICATIONS

Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R, Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime AFRESAS® (inhaled Technosphere® insulin) and basal insulin versus premixed insulin ADA 2009; Poster 551.
http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published on Jan. 27, 2011 as per "Wayback Engine".
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.com/startingoninsulin/whatisinulin.aspx, pp. 1-3. in Non-Final Offfice Action dated May 22, 2014 for U.S. Appl. No. 13/797,657 and in Non-Final Office Action dated May 22, 2014 for U.S. Appl. No. 12/883,369.
International Search Report for PCT International Application No. PCT/US2010/055323 filed on Nov. 3, 2010.
Written Opinion dated Jul. 1, 2013 for International Application No. PCT/US2013/032162 filed on Mar. 15, 2013.
International Search Report dated Jun. 21, 2010 for International Application No. PCT/US2010/027038 filed on Mar. 11, 2010.
Written Opinion for International Application No. PCT/US2011/060057 filed on Nov. 9, 2011.
International Search Report dated Mar. 18, 2013 for International Application No. PCT/US2012/061749 filed on Oct. 24, 2012.
International Search Report dated Jun. 20, 2012 for International Applicaion No. PCT/US2012/031695 filed on Mar. 30, 2012.
International Search Report dated Nov. 19, 2014 for International Application No. PCT/US2014/049817 filed on Aug. 5, 2014.
International Search Report for International Application No. PCT/US2010/020448 filed on Jan. 8, 2010.
International Search Report dated Mar. 11, 2010 for International Application No. PCT/US2009/069745 filed on Dec. 29, 2009.
International Search Report dated Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavor Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Chemical Abstracts, vol. No. 114(22), Abstract No. 214519x (1990).
Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing health-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).
Combettes and Kargar, C, Newly Approved and Promising Antidiabetic Agents. Therapie, Jul.-Aug. 2007: 62(4):293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).

(56) References Cited

OTHER PUBLICATIONS

Cricket TM Single-Use Inhalers [on-line]. MannKind Technologies Website, posted in 2011, [retrieved on Jul. 30, 2012]. Retrieved from the Internet. <URL:mannkindtechnologies,com/DeviceTechnology/CricketSingleUseInhalers.aspx>.

Crosby, J. "Dog Normals", <http://vetmedicine.about.com/od/diseasesconditionsfaqs/tp/TP_dogfacts.htm>, copyright 2013.

Cruetzfeldt et al. "Glucagonostatic actions and reduction of fasting hyerglycemia by exogenous glucagon-like peptide i(7-36) amide in type 1 diabetic patients." Diabetes Care 19:580, 1996.

D'Alessio et al., Elimination of the action of glucagon-like peptide 1 causes an impairment of glucose tolerance after nutrient ingestion by healthy baboons. J. Clin. Invest., 97:133-38 (1996).

Database adisinsight, "Gucagon-like peptide-1 inhalation-MannKind Corporation", Database accession No. 2009:1048 Abstract.

Davis "Postprandial Physiology and the Pathogenesis of Type 2 Diabetes Mellitus." Insulin, vol. 3, Apr. 1, 2008, pp. 132-140.

De Heer et al. "Sulfonylurea compounds uncouple the glucose dependence of the insulinotropic effect of glucagon-like peptide-1." Diabetes 56:438, 2007.

Deacon "Therapeutic strategies based on glucagon-like peptide 1." Diabetes. Sep.;53(9):2181-9, 2004.

Deacon et al., "Glucagon-like peptide 1 undergoes differential tissue-specific metabolism in the anesthetized pig", Am. J. Physiol. 271 (Endocrino. Metab. 34): E458-E464, 1996.

Decode study group. "Glucose tolerance and mortality: comparison of WHO and American Diabetes Association diagnostic criteria." Lancet. Aug. 21, 1999;354(9179):617-21.

DedicatedPhase, "Preclinical Trials and Research", <http://www.dedicatedphase1.com/preclinical-research.html>, copyright 2006-2011, p. 1.

Definition of analog from http://cancerweb.ncl.ac.uk/omd/about.html, pp. 1-5. Accessed by Examiner on Jul. 7, 2005 and cited in Office Action dated Jul. 26, 2013 in U.S. Appl. No. 12/830,557.

Del Prato S "Unlocking the opportunity of tight glycemic control" Diabetes Obesity and Metabolism 7:S1-S4, 2005.

Delgado-Aros et al. "Effect of GLP-1 on gastric volume, emptying, maximum volume ingested and postprandial symptoms in humans." Am J Physiol Gastrointest Liver Physiol 282:G424, 2002.

Diabetes: Counting Carbs if You Use Insulin, WedMD, http://diabetes.webmd.com/carbohydrate-counting-for-people-who-use-insulin#m Oct. 1, 2010.

Diez et al. "Inhaled insulin—a new therapeutic option in the treatment of diabetes mellitus" Expert Opin. Pharmacother., 2003, 4, 191-200.

Dorwald, F.A. Side reactions in organic synthesis. Wiley, (2005).

Doyle et al. "Glucagon-like peptide-1." Recent Prog Horm Res. 2001;56:377-99.

Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.

Drucker "Development of glucagon-like peptide-1-based pharmaceuticals as therapeutic agents for the treatment of diabetes." Curr Pharma Design 7:1399, 2001.

Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.

Drug Delivery, Easing the drug delivery route, Jun. 2006, Pharmaceutical & Medical Packaging News, Canon Communications.

Dungan et al., Glucagon-like peptide 1-based therapies for type 2 diabetes: a focus on exntadtide. Clinical Diabetes, 23: 56-62 (2005).

Dunn, "Zinc-ligand interactions modulate assembly and stability of the insulin hexamer", Biometals, 18(4):295-303 (2005).

Edelman "Type II Diabetes Mellitus." Adv Int Med, 43:449-500, 1998.

Edited by Fukushima, Masanori, "Arterial Sclerosis," Merck Manual 17th, Japanese Edition, NIKKEI BP Corp., p. 1659-1663, 1999.

Edwards CMB et al. "Cardiovascular and pancreatic endocrine response to glucagon-like peptide-1(7-36) amide in the conscious calf." Exp Physiol 82:709, 1997.

Edwards CMB et al. "Subcutaneous glucagon-like peptide-1(7-36) amide is insulinotropic and can cause hypoglycaemia in fasted healthy subjects." Clinical Science 96:719, 1998.

Edwards et al., Recent advances in pulmonary drug delivery using large, porous inhaled particles. Journal of Applied Physiology, pp. 379-385 (1998).

Eggers et al., Molecular confinement influences protein structure and enhances thermal protein stability. Protein Sci., 10:250-261 (2001).

Ehlers et al. "Recombinant glucagon-like peptide-1 (7-36 amide) lowers fasting serum glucose in a broad spectrum of patients with type 2 diabetes." Horm Metab Res 35:611, 2003.

Eissele et al., Rat gastric somatostatin and gastrin relase: interactions of exendin-4 and truncated glucagon-like peptide-1 (GLP-1) amide. Life Sci., 55(8):629-634 (1994).

Elliot et al., Parenteral absorption of insulin from the lung in diabetic children. Austr. Paediatr. J. 23: 293-297 (1987).

Elrick et al. "Plasma insulin response to oral and intravenous glucose administration." J Clin Endocr 24:1076, 1964.

Engelgau MM "Screening for type 2 diabetes." Diabetes Care 23:1563-1580, 2000.

Engwerda et al., Improved pharmackinetic and pharmacodynamic profile of rapid-acting insulin using needle-free jet injection technology. Diabetes Care, vol. 34, Aug. 2011, pp. 1804-1808.

Erlanger et al., Phosphorous pentoxide as a reagent in peptide synthesis. College of Physicians and Surgeons—Columbia Univeristy, vol. 26, pp. 2534-2536 (1960).

Exubera indications, dosage, storage, stability. Http://www.rxlist.com/cgi/generic4/exubera_ids.htm, 2008.

Exubera package insert, p. 1, 2008.

Fadl et al., Effects of MDI spray angle on aerosol penetration efficiency through an oral airway cast. Journal of Aerosol Science, vol. 38, No. 8, pp. 853-864 (2007).

Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).

Farr, S.J. et al., Pulmonary insulin administration using the AERx®system:physiological and physiochemical factors influencing insulin effectiveness in healthy fasting subjects. Diabetes Tech. Ther. 2:185-197, 2000.

Fehmann et al. "Cell and molecular biology of the incretin hormones glucagon-like peptide-1 and glucose-dependent insulin releasing polypeptide." Endocrine Reviews 16:390, 1995.

Ferrin et al, Pulmonary retention of ultrafine and fine particles in rats. Am. J. Repir. Cell Mol. Biol., pp. 535-542 (1992).

Festa et al., "LDL particle size in relation to insulin, proinsulin, and insulin sensitivity" Diabetes Care, 22(10):1688-1693 (1999).

Forst et al., "Metabolic Effects of Mealtime Insulin Lispro in Comparison to Glibenclamide in Early Type 2 Diabetes", Exp. Clin. Endocrinol. Diabetes, 2003, 111, 97-103.

Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.

Galinsky et al., A synthesis of diketopiperazine's using polyphosphoric acid. Journal of the American Pharmaceutical Association, vol. 46, No. 7, pp. 391-393 (1957).

Garber, "Premixed insulin analogues for the treatment of diabetes mellitus", Drugs, 66(1):31-49 (2006).

Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.

Garg SK, Kelly W, Freson B, et al. Treat-to-target Technosphere® insulin in patients with type 1 diabetes. ADA 2011; Abstract 941-P.

Garg SK, McGill JB, Rosenstock J, et al. Technosphere® insulin vs insulin lispro in patients with type 1 diabetes using multiple daily injections. ADA, Abstract 917-P (2011).

(56) References Cited

OTHER PUBLICATIONS

Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1 (accessed Apr. 24, 2015).
Glucophage Product Insert. Jan. 2009.
Glucotrol Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.
Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).
Lian et al. "A Self-Complimentary Self-Assembling Microsphere System: Application for Intravenous Delivery of the Antiepilpetic and Neuroprotectant Compound Felbanate." J Pharm Sci 89:867-875, 2000.
Lim, "Microencapsulation of Living Cells and Tissues", J. Pharm. Sci., 70: 351-354 (1981).
Linder et al., Increase in serum insulin levels is correlated with lung distribution after pulmonary delivery of Technosphere/Insulin. Diabetologia, No. 46, A277 (2003).
Liu et al., "Pulmonary delivery of free and liposomal insulin", Pharmaceuticals Res. 10:228-232, 1993.
Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.
Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Exendin-4, a new peptide from Heloderma suspectum venom, potentiates cholecystokinin-induced amylase release from rat pancreatic acini. Regulatory Peptides, 41:149-56, 1992.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
Mannkind Corporation "Postprandial hyperglycemia: clinical significance, pathogenesis and treatment." MannKind Corporation Monograph. 2009.
MannKind Corporation, Pulmonary Delivery: Innovative Technologies Breathing New Life into Inhalable Therapeutics, www..ondrugdelivery.com, 2006.

(56) References Cited

OTHER PUBLICATIONS

Burcelin et al., Long-lasting antidiabetic effect of a dipeptidyl peptidase IV-resistant analong of glucagon-like peptide-1. Metabolism, vol. 48, No. 2, pp. 252-258 (1999).
Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokinetic/pharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in pk studies using AFRESA® (Technosphere® insulin [TI]) ADA 2009; Poster 1451.
Marshall "Preventing and detecting complications of diabetes." BMJ 333:455, 2006.
Mastrandrea "A breath of life for inhaled insulin: severe subcutaneous insulin resistance as an indication." Pediatric Diabetes 2010: 11: 377-379.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.
McElduff A et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mendes et al., A non-dimensional functional relationship for the fine particle fraction produced by dry powder inhalers, Aerosol Science 38, pp. 612-624 (2007).

Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Montrose-Rafizadeh et al., Diabetes, 45(Suppl. 2):152A, 1996.
Moren, Aerosols in Medicine (2nd Ed.), Elsevier, pp. 321-350 (1993).
Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund E et al. "GLP-1 slows solid gastric emptying and inhibits insulin, glucagon, and PYY release in humans." Am J Physiol (Regulatory Integrative Comp Physiol 46):R910, 1999.
Naslund E et al. "Prandial subcutaneous injections of glucagon-like petide-1 cause weight loss in obese human subjects." Br J Nutrition 91:439, 2004.
International Search Report dated Nov. 21, 2013 for International Application No. PCT/US2013/057397 filed on Aug. 29, 2013.
Eavarone et al., A voxel-based monte carlo model of drug release from bulk eroding nanoparticles. Journal of Nanoscience and Nanotechnology, vol. 10, pp. 5903-5907 (2010).
Marino MT, Cassidy JP, Smutney CC, et al. Improvement in bioavailability of FDKP with the NexGen2A device: Implications for delivery of pulmonary insulin. Diabetes Technology Meeting 2009; poster.
Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279(23):24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.

(56) References Cited

OTHER PUBLICATIONS

Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, Accepted and Received 2007, published on web 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapter 3, pp. 43-56 (2001).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin." Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technospheren™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et Al. Pulmonary delivery of Technosphere™/insulin: Increased bioefficacy and bioavailability in clinical trials using the PDC Medtonen™ inhaler. Proceed Int'l Symp Control Rel Bioact Mater 2000; 27:1000-1001.
Stowell et al. "Development of GLP-1 Technosphere(TM) powder: an inhaled GLP-1 product." Diabetes Technology Meeting, San Francisco, Oct. 2007.
Strack "Inhaled Human Insulin." Drugs of Today 2006, 42 (4): 207-221.

(56) References Cited

OTHER PUBLICATIONS

Sturis et al., GLP-1 deriative liraglutide in rats with beta-cell deficiences: influence of metabolic state on beta-cell mass dynamics. British Journal of Pharmacology, 140: 123-132 (2003).
Svartengren et al., Added External Resistance Reduces Oropharyngeal Deposition and Increases Lung Deposition of Aerosol Particles in Asthmatics. Am. J. Respir. Crit. Care Med., vol. 152, pp. 32-37, 1995.
Sympatecs. Dry Dispersion for Laser Diffraction and Image Analysis, 2011. XP-002586530.
Leone-Bay et al., Innovation in drug delivery by inhalation. Ondrugdelivery, No. 7, pp. 4-8 (2010).
Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.
Telko et al., Dry Powder Inhaler Formulation. Respiratory Care, Sep. 2005, vol. 50, No. 9, 1209-1227.
The American Diabetes Association "Insulin Administration" Diabetes Care, vol. 27, Supplement 1, S106-S109 (2004).
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in non-insulin-dependent diabetes mellitus." Eur J Olin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.
Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.
Tuley et al., Experimental observations of dry powder inhaler dose fluidisation. International Journal of Pharmaceutics, 358, pp. 238-247 (2007).

Utah Valley University. Saponification. © 2009. Available from: <http://science.uvu.edu/ochem/index.php/alphabetical/s-t/saponification/printpage/>.
Vaczek, Accelerating drug delivery firms exploring new drug-delivery routes and devices intently awaiting the commercial launch of Exubera. Pharmaceutical & Medical Packaging News, vol. 14, No. 6 (2006).
Vahl et al. "Effects of GLP-1(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Van Alfen-Van Der Velden et al. "Successful treatment of severe subcutaneou insulin resistance with inhaled insulin therapy", Pediatric Diabetes 2010: 11:380-382.
Vara E et al. "Glucagon-like peptide-1 (7-36) amide stimulates surfactant secretion in human type II pneumocytes." Am J Resp Crit Care Med 163:840-846, 2001.
Vella A et al. "Effect of glucagon-like peptide 1(7-36) amide on glucose effectiveness and insulin action in people with type 2 diabetes." Diabetes 49:611, 2000.
Vella A et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.
Verdich C, et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist. com, Decision News Media SAS (2006).

(56) References Cited

OTHER PUBLICATIONS

Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes 2010.8:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.
Ryan EA et al. "Successful islet transplantation. Continued insulin reserve provides long-term glycemic control." Diabetes 51:2148-2157, 2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function" Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney et al., Bioerodible hydrogels based on photopolymerized poly(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103,1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen activator inhibitor type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.

Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shimada et al. Translocation pathway of the intertracheally instilled ultrafine particles from the lung into the blood circulation in the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, a Statement of the American Diabetes Association", Diabetes Care, Jan. 2005, vol. 28, pp. 186-212.
Singh et al., Use of 125I-[Y39]exendin-4 to characterize exendin receptors on dispersed pancreatic acini and gastric chief cells from guinea pig. Regul. Pept. 53 : 47-59 (1994).
Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007." Diabetes Tecnology & Therapeutics, vol. 9, Supplement 1, pp. S1-53. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Non-Final Offfice Action dated May 22, 2014 for U.S. Appl. No. 13/797,657 and Non-Final Office Action dated May 22, 2014 for U.S. Appl. No. 12/883,369.
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).

(56) References Cited

OTHER PUBLICATIONS

Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Boss et al. "Prandial Insulin: Is Inhaled Enough?" Drug Development Research 69(3):138-142 (2008).
Boss A H, Petrucci R, Lorber D. Coverage of prandial insulin requirements by means of an ultra-rapid-acting inhaled insulin. Journal of diabetes science and technology 2012;6:773-779.
Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.
Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.
Boss AH, Evans, SH, Ren, H, et al. Superior post prandial glucose control in patients with type 1 diabetes when using prandial technosphere insulin compared to NovoLog. Diabetologia 2006; Abstract 181.
Boss AH, Marino MT, Cassidy JP, et al. C-peptide correction method to determine exogenous insulin levels in pharmacokinetic studies using Technosphere® insulin. Diabetologia 2009; 52 (suppl 1).
Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Brange et al., "Insulin Structure and Stability", Pharm Biotechnol, 5:315-50 (1993).
Bray "Exanatide" Am J Health-Sys Pharm 63:411, 2006.
Brownlee et al. "Glycemic variability: a hemoglobin A1c-independent risk factor for diabetic complications." JAMA 295:1707, 2006.
Bruce, D.G. et al. "Physiological importance of deficiency of early prandial insulin secretion in non-insulin-dependent diabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Camilleri, Clinical Practice: Diabetic Gastroparesis. The New England Journal of Medicine, 356: 820-829 (2007).
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.
Cassidy J, Baughman RA, Tonelli G, et al. Use of rapid acting insulin analog as the baseline infusion during glucose clamping improves pharmacokinetic evaluation. ADA 2007; 56: Abstract 602-R.
Cassidy JP, Baughman RA, Schwartz SL, et al. AFRESA® (Technosphere® insulin) dosage strengths are interchangeable ADA 2009; Poster 433.
Cassidy JP, Marino MT, Amin N, et al. Lung deposition and absorption of insulin from AFRESA® (Technosphere® insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life Considerations on shape and function." Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3): 203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-467.
Chase et al., "Redefining the clinical remission period in children with type 1 diabetes", Pediatric Diabetes, 2004, 5, 16-19.
Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
"An inhaled insulin formulation (Technosphere Insulin) effectively improves glycaemic control in patients with type 2 diabetes mellitus." Inpharma Weekly, vol. 1522, Jan. 28, 2006, p. 8.

(56) References Cited

OTHER PUBLICATIONS

ACTOS Product Insert. Aug. 2008.
Adjusting Mealtime Insulin Doses. BD Diabetes. http://www.bd.com/diabetes/page.aspx?cat=7001&id=7280 (2014).
Ahren "GLP-1 and extra-islet effects." Horm. Med Res 36:842, 2004.
Ahren B et al. "Characterization of GLP-1 effects on b-cell function after meal ingestion in humans." Diabetes Care 26:2860,2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.
Alabraba et al. Diabetes Technology & Therapeutics. Jul. 2009, 11(7): 427-430.
Alcohols limited. Alcohol speciality solvents—Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine, vol. 101, No. 11, p. 2395-2401 (2007).
American Diabetes Association, "Standards of medical care in diabetes—2009", Diabetes Care, Jan. 2009, 32 Suppl 1: S13-61.
Amin N, Boss AH, Petrucci R, et al. Pulmonary functions (over 2 years) in diabetic subjects treated with AFRESA® or usual antidiabetic treatment ADA 2009; Poster 570.
Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.
Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.
Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.
Angelo et al., Technosphere Insulin: Defining the Role of Technosphere Particles at the Celluar Level. J. Diabetes Sci. Technol., vol. 3, Issue 3, pp. 545-554 (2009).
Angelo et al. Technosphere® insulin inhalation powder: Defining the mechanism of action. ADA 2008; 57: Poster 428-P.
Antosiewiez et al., Prediction of pH-dependent properties of proteins. J Mol. Biol., 238:415-436 (1994).
Arakawa et al., Preferential interactions determine protein solubility in three-component solutions: the MgCl2 system. Biochemistry, 29:1914-1923 (1990).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin ispro at meal-times" 2005 Diabetes UK, Diabetic Medicine, 23, 46-52.
Atherton, F. et al. "Synthesis of 2(R)-A3(S)-Acylamino-2-OXO-1-Azetidinyloxy U-Acetic Acids." Tetrahedron, vol. 40, No. 6, Jan. 1, 1984, pp. 1039-1046.
Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Drucker et al., Minireview: The glucagon-like peptides. Endocrinology, vol. 142, No. 2, pp. 521-527 (2001).
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al., "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363,1998.
Bensch et al., Absorption of intact protein molecules across the pulmonary air-tissue barrier, Science 156: 1204-1206 (1967).
Berge et al. "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.

(56) References Cited

OTHER PUBLICATIONS

Bergeron et al. "Macromolecular Self-Assembly of Diketopiperazine Tetrapeptides." J. Am. Chem. Soc. 116, 8479-8484, 1994.
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Laube et al., The lung as an alternative route for delivery for insulin in controlling postrprandial glucose levels in patients with diabetes. Chest, Preliminary Report 114 (6) : 1734-1739 (1998).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).
Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro." Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.
Rave et al. "Time-action profile of inhaled insulin in comparison with subcutaneously injected insulin lispro and regular human insulin." Diabetes Care 28:1077, 2005.
Rave K, Heise T, Pfuetzner A, et al. Assessment of dose-response characteristics for a new pulmonary insulin formulation and inhaler. Exp Clin Endocrinol Diabetes 2000; 108:S161.
Rave K, Potocka E, Boss AH, et al. Pharmacokinetics and linear exposure of AFRESA™ compared with the subcutaneous injection of regular human insulin Diabetes, Obesity and Metabolism 2009; 11:715-720.
Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.
Razavi et al. "TRPVI+ sensory neurons control beta cell stress and islet inflammation in autoimmune disease." Cell 127:1123, 2006.
Retrieved from website: http://groups.molbiosci.northwestern.edu/holmgren/Glossary/Definitions/Def-P/placebo.html, 1 page, Retrieved on Mar. 12, 2013.
Rhodes et al. "Technosphere: Microspherical Particles from Substituted Diketopiperazines for Use in Oral Drug Delivery." 208th ACS National Meeting, Aug. 1994.

(56) References Cited

OTHER PUBLICATIONS

Richardson et al. "Technosphere Insulin Technology." Diabetes Technology & Therapeutics, vol. 9, Supplement 1, pp. S65-S72, 2007.

Richardson PC, Potocka E, Baughman RA, et al. Pharmacokinetics of Technosphere® insulin unchanged in patients with chronic obstructive pulmonary disease. Diabetologia 2009; 52 (suppl 1).

Richter et al. "Characterization of glucagon-like peptide-1(7-36)amide receptors of rat membranes by covalent cross-linking." FEBS Letters 280:247, 1991.

Richter et al. "Characterization of receptors for glucagon-like peptide-1 (7-36)amide on rat lung membranes." FEBS Letters 267:78, 1990.

Riddle "Combining Sulfonylureas and Other Oral Agents." Am J Med, 2000, vol. 108(6A), pp. 15S-22S.

Riddle et al. "Emerging therapies mimicking the effects of amylin and glucagon-like peptide 1." Diabetes Care 29:435, 2006.

Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.

Rosen et al., Substance P microinjected into the periaqueductal gray matter induces antinociception and is released folloing morphine administration. Brain Research, 1001: 87-94 (2004).

Rosenmund et al., Diketopiperazines from Leuchs Anhydrides. Angew Chem Intern. Edit. vol. , No. 2 (1970).

Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.

* cited by examiner

Table 2. Schedule of Treatments

| Procedure | Day | | | | | | | |
|---|---|---|---|---|---|---|---|---|
| Bleed | -3 | | | 28 | | | | |
| Vaccination | | 0 | 14 | | | | | |
| Challenge | | | | | 34 | | | |
| Tissue Harvest | | | | | | | 37 | 40 | 42 |

FIGURE 1

Table 3.

| Group | #Mice | Route | Dose | #Doses | Volume |
|---|---|---|---|---|---|
| Placebo | 12 | IM | PBS[a] | 2 | 40ul |
| Vac-Powder | 12 | IPu-Insufflation | 500ug/25ug rHA[b] | 2 | Powder |
| Vac-Liquid | 12 | IM | 500ug/25ug rHA[c] | 2 | 40ul | a: Phosphate buffer Saline; b: Approx. 90% of dose delivered; c: Greater than 95% of dose delivered; IM: intramuscular; IPu: intrapulmonary.

FIGURE 2

INHALABLE VACCINE COMPOSITIONS AND METHODS

CROSS REFERENCE TO RELATED APPLICATIONS

This application is a 371 of PCT/US2013/066969, filed Oct. 25, 2013, which claims the benefit of U.S. Provisional Patent Application Ser. No. 61/719,308, filed Oct. 26, 2012, the contents of each of which is incorporated herein by reference in its entirety.

TECHNICAL FIELD

Methods and compositions are disclosed for vaccinating a subject against disease. In particular, the compositions are inhalable dry powders suitable and useful for preventing and/or treating diseases caused by microorganisms, for example, microorganisms such as the influenza virus and other viral, parasitic or bacterial infections using an inhalation system. In particular, the method comprises the administration of a composition comprising single or multiple native or recombinant antigens, native particles or subunits or virus-like particles (VLPs) displaying homologous or heterologous antigens and/or specific peptide fragments and/or derivatives thereof into the lungs, pulmonary circulation and/or nasal cavities by oral or nasal inhalation using a dry powder drug delivery system.

BACKGROUND

Drug delivery systems for the treatment of disease or prophylactic vaccination for the prevention of disease which introduce active ingredients into the body are numerous and include oral, intranasal, transdermal, subcutaneous, intramuscular and intravenous administration. While these systems have been used for quite a long time and can deliver sufficient medication for the treatment or prevention of many diseases, there are numerous challenges associated with these drug delivery mechanisms, in particular, delivery of biological active agents or immunogenic compositions that should be able to elicit a protective immune response. Delivery of effective amounts of proteins, peptides and nucleic acids to prevent or treat a target disease has been problematic. Many factors are involved in introducing the right amount of the active agent in an appropriate drug composition or vaccine delivery system so that the formulation used contains the proper amount of active agent that can reach its target site(s) of action in order to attain a prophylactic or therapeutically effective response.

Vaccines are the most efficient and cost-effective means for disease prevention and treatment, however they comprise biological active agents which can require special manufacturing and storage conditions. Most vaccines are injectable and either provided in liquid form, or as a powder formulation which is reconstituted with a liquid prior to immunization. Injectable (intradermal, subcutaneous, intramuscular, intraperitoneal, etc.) vaccines can elicit systemic immune responses effectively. In certain cases, local immune responses to the injection are produced as side effects such as secretory immunoglobulin A (IgA or S-IgA) production at the injection site that can reduce the magnitude of the expected/desired target systemic effects, which in turn, does not consistently translate to systemic immunity. Local immune reactions to the injection can also lead to uncomfortable irritation, itching, and swelling. In some situations, booster or repeated injections of the vaccine are required to attain effective immunization as well as co administered adjuvants.

Liquid vaccine formulations often require cold-chain storage and transport to maintain biological activity, potency and therapeutic effectiveness prior to administration, and can also require a trained healthcare professional for their administration, and proper disposal of needle and syringe. Further, the individual being vaccinated may be obliged to visit a clinic or the office of the professional provider. These limitations make immunization campaigns difficult, particularly during a pandemic situation, an intentional release of an infectious agent or in geographic locations where infrastructure for vaccine storage, distribution and delivery is deficient or non-existent.

Thus uninterrupted maintenance of low temperatures within a specified range during storage and transport of vaccines is required to ensure preservation of biological activity and potency. Disruption of the cold chain system may diminish or completely eliminate vaccine efficacy underlying the importance of a fully functional cold chain network while bringing vaccine from producers to immunization sites to preserving product efficacy. Operating and maintaining an effective cold chain network is expensive and susceptible to interruptions, particularly in under-developed regions. In addition, conflict areas and certain developing countries often lack the infrastructure required for a cold chain system. The need of a refrigerated system poses a serious burden for delivering vaccine in conflict zones, developing countries and in emergency situations.

To overcome the limitations of existing injected vaccines, alternative vaccination strategies, for example, mucosal vaccination systems have been evaluated. Mucosal-associated lymphoid tissues (MALT) form the largest mammalian lymphoid organ system, contributing almost 80% of all immunocytes. Mucosal immunization not only induces systemic immunity (IgG and long lasting cell mediated immune response), but also induces local (s-IgA) immunity at the site of mucosal entry (common mucosal immune response). This common mucosal immune system is associated with organ selectivity demonstrated as enhanced memory at the site of mucosal priming. In addition, mucosal delivery is needle-free and painless, so it is likely to improve patient acceptance and is suitable for mass vaccination campaigns. FLUMIST® is an example of a Food and Drug Administration (FDA)-approved intranasal mucosal vaccine for immunizing against the influenza virus which uses a cold-adapted and temperature sensitive live virus as vaccine.

As mentioned above, current methods of manufacturing, transporting/storing and delivering vaccines prior to immunization is burdened by two major factors; 1) the vaccine must be maintained refrigerated prior to immunization and 2) gathering people for mass immunization. In some situations, these factors are critical and create extraordinary situations, including during outbreaks of pandemic influenza such as the 1918 flu (Spanish flu), and influenza A virus subtype H5N1, also known as "bird flu" and the H1N1 also known as "Swine flu."

Pulmonary immunization against airborne pathogens in some cases has been shown useful, because the lungs contain a highly responsive immune system. The utility, effectiveness, and safety of pulmonary vaccination are well established for some agents such as the measles virus with the pioneering studies of Sabin in the early 1980s, and more recently with the mass vaccination campaigns in Mexico and South Africa. Published studies of inhaled vaccines for measles, influenza, and TB, however, have mostly involved nebulization of solutions, a method of administration that can be plagued by poor efficiency, lengthy administration time, and complex equipment. Accordingly, there is a need to develop new compositions and methods for immunizing against diseases, in particular, infectious and pandemic diseases which would provide a stable composition with a prolonged shelf-life in an easy to administer form and dispenser.

SUMMARY

Disclosed herein are stable, dry powder vaccine compositions, which are easy to use as an immunization system for oral or nasal inhalation. The dry powder vaccines can be for self-administration and can be manufactured to treat diseases of different origins. In an exemplary embodiment, the present vaccines are used to prevent and/or treat viral disease, wherein the target antigens are administered using an inhalation system to induce a local immune response and/or a systemic effect to the target antigen resulting in a subject being immunized. The vaccines can be monovalent or multivalent, stable dry powder formulations that can be stored at room temperature for a prolonged period of time. The dry powder formulations increase vaccine efficacy and overcome the limitations of nebulized formulations or injectable vaccines by improving storage conditions and distribution to a population.

Embodiments include an influenza vaccine comprising a dry powder composition comprising a diketopiperazine and an immunogenic components such as influenza virus-like particles, an antigenic protein, an antigenic peptide, fragments of said influenza virus-like particle, a subunit protein or multiple subunit proteins or fragments of said antigenic protein(s), fragments of said antigenic peptide, or combinations thereof. In embodiments the composition can comprise a diketopiperazine microparticle comprising the immunogenic component. In an embodiment the diketopiperazine can be a diketopiperazine salt.

In embodiments the immunogenic component can comprise a hemagglutinin and/or a neuraminidase protein and/or a matrix protein, or peptide or fragments thereof.

In embodiments the immunogenic component can comprise an antigenic protein or peptide such as a neuraminidase derived from influenza virus type A, B or C, or any subtype of influenza A, or fragments thereof or combinations thereof.

In embodiments the immunogenic component can comprise an antigenic protein or peptide such as hemagglutinin derived from influenza A, B or C or any subtype of influenza A, or fragments thereof, or combinations thereof.

In embodiments the immunogenic component can comprise an antigenic protein or peptide such as hemagglutinin A, or another protein of the influenza virus such as NP, M1, M2, NS1, NS2, polymerase subunits PB1, PB2 or PA or fragments thereof or combinations thereof.

In an embodiment the diketopiperazine is 3,6-bis-(N—X-4-aminobutyl)]-2,5-diketopiperazine, wherein X is fumaryl, glutaryl, succinyl, maleyl, malonyl, or oxalyl. In an embodiment the diketopiperazine is 3,6-bis-(N-fumaryl-4-aminobutyl)]-2,5-diketopiperazine.

An embodiment includes an influenza vaccination system, comprising an inhalation system comprising a dry powder inhaler comprising a dry powder formulation comprising microparticles of 3,6-bis-(N-fumaryl-4-aminobutyl)]-2,5-diketopiperazine and an antigen selected from influenza virus protein consisting of hemagglutinin A or neuraminidase A, or other influenza protein and/or combinations thereof. In an embodiment the hemagglutinin A is a recombinant HA3 antigen. In an embodiment the dry powder inhaler is configured as a single use disposable inhaler for self-administration.

Embodiments include a method for immunizing a subject against a virus infection, for example an influenza virus infection, comprising administering to the subject a therapeutically effective amount of a dry powder vaccine comprising a diketopiperazine and an immunogenic component comprising at least one of a VLP, an antigenic protein, an antigenic peptide, fragments of said virus-like particle, or a subunit protein or multiple distinct subunits proteins or fragments of said antigenic protein/s, fragments of said antigenic peptide, or combinations thereof, wherein the vaccine is self-administered by inhalation. In an embodiment the diketopiperazine is 3,6-bis-(N—X-4-aminobutyl)]-2,5-diketopiperazine, wherein X is fumaryl, glutaryl, succinyl, maleyl, malonyl, or oxalyl. In an embodiment the diketopiperazine is 3,6-bis-(N-fumaryl-4-aminobutyl)]-2,5-diketopiperazine. In an embodiment the antigenic peptide is a recombinant HA3 antigen or fragment thereof. Embodiments can further include providing a booster vaccine comprising the influenza vaccine.

In one embodiment, the vaccine comprises a dry powder inhaler and a dry powder composition comprising an antigen, and/or fragments thereof, or combinations thereof for delivery of the antigen to the respiratory tract including the lungs to induce local as well as systemic immune responses. In some embodiments, the dry powder inhaler is disposable and configured for single use. In embodiments herewith, the dry powder vaccine can be a crystalline powder, an amorphous powder and/or combinations thereof. In another embodiment any format of the powder vaccine is delivered via the intradermal route utilizing micro-needles, dissolvable micro-needles or a vaccine patch.

In a particular embodiment, the vaccine composition against viral infections comprises a dry powder comprising diketopiperazine microparticles and an antigen, antibody, fragment thereof, and/or combinations thereof. In one embodiment, the antigens in the vaccine composition comprise Virus-Like Particles (VLP), peptides, proteins, including glycoproteins, and/or fragments of a VLP, antigenic proteins and/or antigenic peptides, or combinations thereof. The dry powder composition comprises highly immunogenic, non-infectious monovalent and/or polyvalent vaccines using an antigen formed from a cell-based manufacturing system, and delivered using a dry powder inhaler.

Embodiments include a dry powder formulation comprising a diketopiperazine and an antigen or antibody for treating influenza. In this embodiment, the vaccine composition comprises an immunogenic VLP, and/or antigenic proteins or peptides thereof wherein the antigenic protein(s) or peptides are viral in nature, including, viral proteins and peptides corresponding to those of influenza virus, including influenza virus A, influenza virus B and influenza virus C. In this embodiment, the vaccine comprises a breath powered, dry powder, single use inhaler comprising a dry powder composition comprising peptide(s), protein(s), glycoprotein(s) and/or combinations therein including, Hemagglutinin (HA) or a subtype thereof selected from subtypes H1, H2, H3, H4, H5, H6, H7, H8, H9, H10, H11, H12, H13, H4, H15, H16, and/or H17, or other mutants thereof, and/or a neuraminidase (NA) or a subtype thereof selected from subtypes N1, N2, N3, N4, N5, N6, N7, N8, N9, and/or N10, or mutants thereof, fragments thereof, or combinations thereof. In one embodiment, an influenza vaccine comprises a dry powder composition comprising a recombinant peptide and/or protein antigen, for example, recombinant HA3 (rHA3) and a diketopiperazine in a single use dry powder inhaler.

In alternate embodiments, the dry powder vaccines can comprise one or more neuraminidase specific antigen(s). In another embodiment, the vaccine composition comprises combinations of HA and NA antigens, or antibodies or fragments thereof against HA or NA and/or their subtypes. In embodiments for treating influenza, the vaccines can be administered as prophylactic in a healthy subject alone, or in combination with a neuraminidase inhibitor, including Oseltamivir (TAMIFLU®) and Zanamivir (RELENZA®) for treatment of influenza A and B viral infections, or M2 inhibitors, including Amantidine (SYMMETREL®) and Rimantadine (FLUMADINE®) or analogs thereof for treatment of influenza A viral infections. In these embodiments, the neuraminidase inhibitor can be administered separately by inhalation or other route of administration.

In one embodiment, an inhalable dry powder vaccine comprising microparticles of a diketopiperazine and a VLP, an antigenic protein, an antigenic peptide, fragments of the VLP, fragments of the antigenic protein, fragments of the antigenic peptide, or combinations thereof, wherein the microparticles of the diketopiperazine are made from, for example, 3,6-bis-(N—X-4-aminobutyl)]-2,5-diketopiperazine, wherein X is fumaryl, glutaryl, succinyl, maleyl, malonyl, oxalyl, or a salt thereof; and a VLP, protein, peptide, glycoprotein and/or fragments thereof.

In one embodiment, an inhalable dry powder vaccine comprises microparticles of a diketopiperazine having the formula 3,6-bis-(N—X-4-aminobutyl)]-2,5-diketopiperazine, wherein X is fumaryl, glutayl, succinyl, maleyl, or malonyl; and a VLP, glycoprotein, protein, peptide, fragments thereof, and/or combinations thereof. In a particular embodiment, the diketopiperazine is fumaryl diketopiperazine (FDKP) having the formula:

or a salt thereof, including disodium, dipotassium, magnesium, lithium, and the like.

In certain embodiments, the vaccine composition comprises a diketopiperazine inhalable dry powder to which is incorporated one or more VLPs, glycoproteins, proteins, peptides and/or peptide fragments; for example those related to influenza viruses. In an embodiment, the influenza VLP, virus glycoprotein, protein, peptide and/or fragments thereof can include one or more Hemagglutinin (HA) proteins or subtype thereof, for example, subtypes H1, H2, H3, H4, H5, H6, H7, H8, H9, H10, H11, H12, H13, H4, H15, H16, and/or H17, or other mutants thereof, and/or a neuraminidase (NA) or subtype thereof, for example, subtypes N1, N2, N3, N4, N5, N6, N7, N8, N9, and/or N10, or mutants thereof, fragments thereof, or combinations thereof. In an embodiment, the antigenic peptides or proteins are H1, H2, H3, H5, N1, N2, N5, N7 and/or N8, fragments thereof or combinations thereof, for example, H3 and N2, H2 and N2, H1 and N1, H5 and N1 and the like. In other embodiments, the VLP, glycoprotein, protein, peptide and/or fragment thereof comprises other influenza proteins such as NP, M1, M2, NS1, NS2 or the polymerase subunits PB1, PB2, and PA or combination thereof.

The amount of an antigen for use in the compositions can be determined by the immunogenicity of the antigen. In some embodiments, the amount of peptide or protein in the compositions can range from about 0.001 μg to more than 1 mg, or 0.001 μg to 1 mg, or 0.01 μg to 1 mg, or 0.1 μg to 0.1 mg, or 0.1 μg to 0.05 mg, or the like. For example, an influenza vaccine can comprise a recombinant HA3 peptide (for example, rHA3; derived from influenza A/Perth/2009 (H3N1)) in amounts ranging from about 0.05 mg to 50 mg of bulk powder with a rHA3 content of approximately 5% (e.g. 0.5 mg powder/0.025 mg rHA3; 500 μg powder/25 μg rHA3). In some embodiments, the amount of dry powder to be administered to a subject can be, for example, greater than 0.5 mg, greater than 1 mg, greater than 2 mg, greater than 5 mg, greater than 10 mg, greater than 15 mg, greater than 20 mg, greater than 30 mg, or the like.

Further embodiments include vaccine delivery systems comprising an inhaler, a unit dose dry powder medicament container, and a powder comprising the microparticles disclosed herein and an immunogen including, for example, one or more antigens. In some embodiments the container can be a cartridge that is loaded into the inhaler; in other embodiments the container is integral with the inhaler. In one embodiment, the delivery system for use with the dry powders includes an inhalation system comprising a high resistance inhaler having air conduits which impart a high resistance to airflow through the conduits for deagglomerating and dispensing the powder. In one embodiment, the inhalation system has a resistance value of, for example, approximately 0.065 to about 0.200 (√kPa)/liters per minute, or 0.1 to about 0.200 (√kPa)/liters per minute, or 0.1 to about 0.150 (√kPa)/liters per minute, or the like. In certain embodiments, the dry powders can be delivered effectively by inhalation with an inhalation system wherein the peak inhalation pressure differential can range from about 2 to about 20 kPa, from about 4 to about 16 kPa, or from about 10 to about 12 kPa, which can produce resultant peak flow rates of about between 7 and 70 liters per minute. In certain embodiments, the inhalation system are configured to provide a single dose by discharging powder from the inhaler as a continuous flow, or as one or more pulses of powder delivered to a patient in, for example, less than 5 seconds, or less than 4 seconds, or less than 3 seconds, or less than 2 seconds or less than 1 second.

In some embodiments disclosed herewith, the dry powder inhaler system comprises a predetermined mass flow balance within the inhaler. For example, a flow balance of approximately 10% to 70% of the total flow exiting the inhaler and into the patient is delivered by one or more dispensing ports, which airflow passes through the area containing the powder formulation, and wherein approximately 30% to 90% air flow is generated from other conduits of the inhaler. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the mouthpiece. In one embodiment, flow rates ranging from about 7 to 70 liters per minute result in greater than 75% of the container or the cartridge contents dispensed in fill masses between 1 and 30 mg. In certain embodiments, an inhalation system as described above can emit a respirable fraction/fill of a powder dose at percentages greater than 40% in a single inhalation, greater than 50%, greater than 60%, greater than 70%, greater than 80%, or greater than 90%, or a range between any of these values.

In particular embodiments, an inhalation system is provided comprising a dry powder inhaler, a dry powder formulation comprising microparticles of fumaryl diketopiperazine having an FDKP trans isomer content between 45% and 65% and one or more immunogens, antigens or active agents. In some aspects of this embodiment of the inhalation system, the dry powder formulation is provided in a unit dose cartridge. Alternatively, the dry powder formulation can be preloaded in the inhaler. In this embodiment, the structural configuration of the inhalation system allows the deagglomeration mechanism of the inhaler to produce respirable fractions greater than 50%; that is, more than half of the powder contained in the inhaler (cartridge) is emitted as particles of less than 5.8 µm. The inhalers can discharge greater than 85% of a powder medicament (e.g., vaccine) contained within a container during dosing. In certain embodiments, the inhalers can discharge greater than 85% of a powder medicament contained in a single inhalation. In one embodiment, the inhalers can discharge greater that 90% of the cartridge contents or container contents in less than 3 seconds at pressure differentials between 2 and 5 kPa with fill masses ranging up to 30 mg, 40 mg, or 50 mg.

In an alternate embodiment, dry powder vaccines as described herein can comprise pharmaceutically acceptable carriers and/or excipients, including amino acids for example, leucine, alanine, glycine, isoleucine, norleucine; sugars, for example, mannitol, xylitol, and the like at amounts ranging from about 0.5% to about 30% by weight, from about 0.9% to about 25% by weight, from about 5% to about 20% by weight, from about 10% to about 15% by weight. Optionally, vaccine compositions can comprise surfactants, including polysorbates, for example, PS 80, TWEEN®s, and the like. Additionally, vaccine compositions can include an adjuvant, an immunodulator or substances that enhance the effectiveness of the vaccine product.

In yet an alternate embodiment, a method for immunizing a subject is provided, comprising administering to the subject a therapeutically or prophylactically effective amount of a dry powder vaccine composition comprising a diketopiperazine and a VLP, for example an influenza virus glycoprotein, protein, peptide selected from HA or NA or a subtype thereof, fragments thereof or combinations thereof; wherein the subject inhales the vaccine composition in a single inhalation. In this embodiment, booster inhalations can be given after, for example, one week, two weeks, three weeks or a month of administration of a first dose.

In an alternate embodiment, the dry powder formulation can be reconstituted with a suitable diluent, for example, saline solution or a buffer, including phosphate buffer for administering the antigen by injection or intradermal application via micro-needles or vaccine patch. In this embodiment, the dry powder formulation is stable at room temperature for an extended period of time compared to current vaccination formulations requiring refrigeration.

BRIEF DESCRIPTION OF THE DRAWINGS

FIG. 1 depicts Table 2, showing the Schedule of Treatments.

FIG. 2 depicts Table 3, showing the Group, number of mice, route of administration, dose, number of doses, and dose volume.

DEFINITION OF TERMS

Prior to setting forth the invention, it may be helpful to provide an understanding of certain terms that will be used hereinafter:

Analog: As used herein, an "analog" includes compounds having structural or functional similarity to another compound. For example, the anti-viral compound acyclovir is a nucleoside analogue and is structurally similar to the nucleoside guanosine which is derived from the base guanine. Thus, acyclovir mimics guanosine (is biologically analogous with) and interferes with DNA synthesis by replacing (or competing with) guanosine residues in the viral nucleic acid and prevents translation/transcription. Thus, compounds having structural similarity to another (a parent compound) that mimic the biological or chemical activity of the parent compound are analogs. There are no minimum or maximum numbers of elemental or functional group substitutions required to qualify a compound as an analog provided the analog is capable of mimicking, in some relevant fashion, either identically, complementarily or competitively, with the biological or chemical properties of the parent compound. Analogs can be, and often are, derivatives of the parent compound (see "derivative" infra). Analogs of the compounds disclosed herein may have equal, lesser or greater activity than their parent compounds.

Derivative: As used herein, a "derivative" is a compound made from (or derived from), either naturally or synthetically, a parent compound. A derivative may be an analog (see "analog" supra) and thus may possess similar chemical or biological activity. However, unlike an analog, a derivative does not necessarily have to mimic the biological or chemical activity of the parent compound. There are no minimum or maximum numbers of elemental or functional group substitutions required to qualify a compound as a derivative. For example, while the antiviral compound ganciclovir is a derivative of acyclovir, ganciclovir has a different spectrum of anti-viral activity and different toxicological properties than acyclovir. Derivatives of the compounds disclosed herein may have equal, less, greater or even distinct activities when compared to their parent compounds.

Diketopiperazine: As used herein, "diketopiperazine" or "DKP" includes diketopiperazines and salts, derivatives, analogs and modifications thereof falling within the scope of the general Formula 1, wherein the ring atoms $E_1$ and $E_2$ at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

$$\underset{R_2}{\overset{O}{\diagdown}}\underset{E_2}{\overset{E_1}{\diagup}}\underset{O}{\overset{R_1}{\diagdown}}$$ Formula 1

Diketopiperazines, in addition to making aerodynamically suitable microparticles, also facilitate the delivery of drugs by enabling absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules. Diketopiperazines may also facilitate absorption of an associated drug.

In one embodiment, the diketopiperazine is 3,6-di(fumaryl-4-aminobutyl)-2,5-diketopiperazine (fumaryl diketopiperazine, FDKP). The FDKP can comprise microparticles in its acid form or salt forms which can be aerosolized or administered in a suspension.

In another embodiment, the DKP is a derivative of 3,6-di(4-aminobutyl)-2,5-diketopiperazine, which can be formed by (thermal) condensation of the amino acid lysine. Exemplary derivatives include 3,6-bis-(N—X-4-aminobutyl)]-2,5-diketopiperazine; wherein X is fumaryl, glutaryl, succinyl, maleyl, malonyl, or oxalyl and the compounds are 3,6-di(succinyl-4-aminobutyl)-, 3,6-di(maleyl-4-aminobutyl)-, 3,6-di(glutaryl-4-aminobutyl), 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461; 5,503,852; 6,071,497; 6,331,318; 8,227,409; 8,227,409; each of which is incorporated herein by reference for all that they teach regarding diketopiperazines and diketopiperazine-mediated drug delivery). The use of DKP salts is described in U.S. Pat. Nos. 7,820,676 and 8,278,308, which are hereby incorporated by reference for all they teach regarding diketopiperazine salts. Pulmonary drug delivery using DKP microparticles is disclosed in U.S. Pat. No. 6,428,771, which is hereby incorporated by reference in its entirety. Nasal drug delivery using DKP microparticles is disclosed in U.S. Pat. No. 7,833,550 which is hereby incorporated by reference in its entirety. Further details related to adsorption of active agents onto crystalline DKP particles can be found in U.S. Pat. Nos. 7,799,344 and 7,803,404, which are hereby incorporated by reference in their entirety.

Drug delivery system: As used herein, "drug delivery system" refers to a system for delivering one or more active agents.

Dry powder: As used herein, "dry powder" refers to a fine particulate composition that is not suspended or dissolved in a propellant, liquid, or other carrier. It is not meant to necessarily imply a complete absence of all water molecules.

Immunogen: As used herein, "immunogen" refers to a molecule that induces an immune response when administered to subject (e.g., human or non-human animal), including inducing the production of antibodies or expansion of antigen-specific T cells in the subject against the molecule after administration. It can be naturally derived, produced by a recombinant process, or by a synthetic process.

Microparticles: As used herein, the term "microparticles" includes particles of generally 0.5 to 100 microns in diameter and particularly those less than 10 microns in diameter. Various embodiments will entail more specific size ranges. The microparticles can be assemblages of crystalline plates with irregular surfaces and internal voids as is typical of those made by pH controlled precipitation of the DKP acids. In such embodiments the active agents can be entrapped by the precipitation process or coated onto the crystalline surfaces of the microparticle. The microparticles can also be spherical shells or collapsed spherical shells comprised of DKP salts with the active agent dispersed throughout. Typically such particles can be obtained by spray drying a co-solution of the DKP and the active agent. The DKP salt in such particles can be amorphous. The forgoing descriptions should be understood as exemplary. Other forms of microparticles are contemplated and encompassed by the term.

Pulmonary inhalation: As used herein, "pulmonary inhalation" is used to refer to administration of pharmaceutical preparations by inhalation so that they reach the lungs and in particular embodiments the alveolar regions of the lung. Typically inhalation is through the mouth, but in alternative embodiments in can entail inhalation through the nose.

Therapeutically effective amount: As used herein, the term "therapeutically effective amount" of a composition, when administered to a human or non-human patient, to provide a therapeutic or prophylactic benefit such as amelioration of symptoms or prevention of a transmissible disease, e.g., an amount effective to stimulate the production and secretion of antibodies that neutralize an infective agent as well as a T lymphocyte response against the agent. Thus a therapeutically effective amount of a composition is also an amount sufficient to prevent the onset of symptoms of a disease or reduce their severity.

DETAILED DESCRIPTION

In embodiments described herein, there is provided a dry powder immunization system and methods that allow for improved delivery of vaccines to a subject for self-administration and which vaccines have an increased shelf-life and can be stored at room temperature for various periods of times while maintaining efficacy. The present vaccine compositions are for inhalation using a dry powder inhaler which can be self administered without the need to visit a clinic, nurse, or a physician. In particular, the vaccine compositions are intended for the treatment and prevention of transmissible diseases including viral infections such as influenza.

In one embodiment, dry powder vaccine compositions comprise a diketopiperazine and one or more antigenic components, including virus-like particles (VLPs), immunogenic proteins, peptides or fragments of the viral proteins. In certain embodiments, antigenic molecules which can also be delivered by the methods herein include, antigens derived from pathogenic agents such as parasites, or bacteria, tumor antigens, allergens or self-antigens; or antibodies thereof, can be used to vaccinate or treat against corresponding diseases.

In an exemplary embodiment, the vaccine composition comprises a dry powder comprising a VLP and a diketopiperazine selected from 3,6-di(fumaryl-4-aminobutyl)-2,5-diketopiperazine (fumaryl diketopiperazine, FDKP); 3,6-di(succinyl-4-aminobutyl)-2,5-diketopiperazine, 3,6-di(maleyl-4-aminobutyl)-2,5-diketopiperazine, 3,6-di (glutaryl-4-aminobutyl)-2,5-diketopiperazine, 3,6-di (malonyl-4-aminobutyl)-2,5-diketopiperazine, 3,6-di (oxalyl-4-aminobutyl)-2,5-diketopiperazine or derivatives of analogs thereof.

In a particular embodiment, fumaryl diketopiperazine 3,6-bis-(N-fumaryl-4-aminobutyl)]-2,5-diketopiperazine (FDKP) is used as the diketopiperazine for pulmonary inhalation applications:

$$\text{[FDKP chemical structure]}$$

In this embodiment, the diketopiperazine can be in crystalline or amorphous dry powder form or combinations thereof. In one embodiment, the dry powder composition can comprise the disodium salt of the diketopiperazine or other salts including, dipotassium, magnesium, lithium and the like.

In embodiments utilizing FDKP in the compositions, FDKP provides a beneficial microparticle matrix because it has low solubility in acid, but is readily soluble near neutral or at basic pH. These properties allow FDKP to crystallize and the crystals to self-assemble into form microparticles under acidic conditions. The particles dissolve readily under physiological conditions where the pH is neutral. As noted, microparticles having a diameter of between about 0.5 and about 10 microns can reach the lungs, successfully passing most of the natural barriers. Particles in this size range can be readily prepared from FDKP as a crystalline powder, an amorphous powder, or combinations thereof by several methods.

In a particular embodiment, the vaccine composition against viral infections is provided comprising a dry powder composition comprising diketopiperazine microparticles and an antigen, antibody, fragment thereof, and/or combinations thereof. In one embodiment, the antigens in the vaccine composition comprise VLPs comprising peptides, proteins, including glycoproteins, and/or individual antigenic components or fragments of a VLP, fragments of the antigenic proteins and/or antigenic peptides, or combinations thereof. In this embodiment, the dry powder vaccine composition comprises highly immunogenic, non-infectious monovalent and/or polyvalent vaccines using an antigen produced from a cell-based manufacturing system, and delivered using a dry powder inhaler for single use.

In an embodiment inhaled FDKP particles carry the immunogens to the lungs or nasal cavities, wherein the particles dissolve immediately upon contact with wet tissue surfaces at the prevailing physiological pH due to FDKP's characteristics consisting of high solubility at pH ≥6. Once the particles are dissolved, the immunogenic material is available for local and systemic absorption. Active factors, including, nucleic acids, proteins and peptides ranging in molecular weight from 300 to 100,000 Da can be administered in the vaccine compositions and are absorbed readily. FDKP delivered to the lungs is absorbed, but is not metabolized and is excreted intact, primarily in urine. FDKP does not directly facilitate drug absorption, but functions solely as the particle matrix.

Exemplary FDKP powders can be delivered using patient friendly, breath-powered inhalers for self-administration and can be configured for single use. In use, a patient's inhalation effort generates the air flow necessary to fluidize, de-agglomerate, and disperse the dry powders from the inhaler with efficiency greater than 90% powder emission from the inhaler. Timing and/or coordination of the inhalation effort with the powder dispersion is not required. In an embodiment, this delivery system comprises high air flow resistance rigid conduits that change the direction of flow at angles that promote deagglomeration. This feature keeps the powder moving slowly during delivery to reduce unwanted throat impaction and promote deep lung deposition. Additionally, the dry powder inhalation system can be designed and configured to prevent powder dispersion during reverse air flow, for example, if a patient accidentally exhales into the device when in use so as to prevent loss of, for example, the vaccine dose being administered. The inhalation system provides consistent delivery. Powder dispersion from these devices begins with the onset of the inhalation effort and ends quickly within approximately 300-500 ms, ensuring proper delivery even with a short or interrupted patient inhalation.

In embodiments described herewith, an inhalation system for pulmonary delivery by nasal or oral inhalation is provided, comprising a dry powder inhaler having rigid air conduits and high resistance to airflow characteristics which delivers a vaccine formulation at pressure differentials greater than 2 kPa; wherein the vaccine formulation comprises a dry powder comprising a diketopiperazine and an antigen or antibody for immunizing a subject against the influenza virus and the vaccine formulation is self-administered by a subject in a single inhalation. In this embodiment, the vaccine composition comprises immunogenic material(s), for example, VLPs, and/or antigenic proteins or peptides thereof, wherein the antigenic protein or peptides are selected for one or more viruses, including, native or recombinant viral glycoproteins, proteins and peptides isolated or derived from an influenza virus, including influenza virus A, influenza virus B and influenza virus C. Non-limiting examples of VLPs that can be incorporated into the formulations and systems as described herein include those disclosed in U.S. Patent Publication Nos. 20080031895; 20090022762 and 20110212128. In this embodiment, the vaccine comprises a breath powered, dry powder, single use inhaler comprising a dry powder formulation comprising a peptide, protein and/or glycoprotein, including, Hemagglutinin (HA) or subtype thereof selected from subtypes H1, H2, H3, H4, H5, H6, H7, H8, H9, H10, H11, H12, H13, H4, H15, H16, and/or H17, or other mutants thereof, and/or a neuraminidase (NA) or subtype thereof selected from subtypes N1, N2, N3, N4, N5, N6, N7, N8, N9, and/or N10, or mutants thereof, fragments thereof, or combinations thereof. In another embodiment, the formulation (e.g., VLP) comprises additional influenza proteins such as NP, M1, M2, NS1, NS2 or the polymerase subunits PB1, PB2, and PA or combination thereof. In an example embodiment, an influenza vaccine comprises a dry powder composition comprising a recombinant peptide and/or protein antigen, for example, recombinant HA3 (rHA3) and a diketopiperazine in a single use dry powder inhaler. In one embodiment, the diketopiperazine comprises microparticles of, for example, fumaryl diketopiperazine or disodium salt of fumaryl diketopiperazine.

In alternate embodiments, the dry powder vaccines can comprise one or more neuraminidase related antigen(s). In another embodiment, the vaccine composition comprises combinations of HA and NA antigens, or antibodies or fragments thereof against HA or NA and/or their subtypes. In embodiments for treating influenza, the vaccines can be administered as prophylactic in healthy subject alone, or in combination with a neuraminidase inhibitor, including Oseltamivir (TAMIFLU®) and Zanamivir (RELENZA®) for treatment of influenza A and B viral infections, or M2 inhibitors, including Amantidine (SYMMETREL®) and Rimantadine (FLUMADINE®) or analogs thereof for treatment of influenza A viral infections. In these embodiments, the neuraminidase inhibitor can be administered separately by inhalation or another route of administration.

In further embodiments, there is provided a drug delivery systems comprising an inhaler, a unit dose dry powder medicament container, for example, a reservoir configured to hold a dry powder, and a dry powder comprising microparticles disclosed herein and an immunogen or antigen including, an influenza virus particle antigen, hemagglutinin A and neuraminidase and/or fragments thereof. In one embodiment, the delivery system for use with the dry powders includes an inhalation system comprising a high resistance inhaler having air conduits which impart a high resistance to airflow through the conduits for deagglomerating and dispensing the powder. In one embodiment, the inhalation system has a resistance value of, for example, approximately 0.065 to about 0.200 ($\sqrt{kPa}$)/liter per minute. In certain embodiments, the dry powders can be delivered effectively by inhalation with an inhalation system wherein the peak inhalation pressure differential can range from about 2 to about 20 kPa, which can produce resultant peak flow rates of about between 7 and 70 liters per minute. In certain embodiments, the inhalation system are configured to provide a single dose by discharging powder from the inhaler as a continuous flow, or as one or more pulses of powder delivered to a patient.

In one embodiment, there is provided a vaccine composition comprising an anti-infective composition against bacteria that can produce disease, including bacteria use as biological warfare agents such as anthrax bacteria. In an example embodiment, the vaccine comprises a dry powder composition composition for inhalation comprising diketopiperazine particles and an immunogenic peptide either from the bacteria, or prepared separately from the bacteria. In one embodiment, for example, the dry powder vaccine composition comprises fumaryl diketopiperazine microparticles and an antigen; wherein the antigen is an immunogenic peptide, for example, a protective antigen or PA peptides. In another embodiment, an inhalable dry powder vaccine composition for immunizing against bacteria including, anthrax or any infectious bacteria comprises particles of a diketopiperazine and antibodies and/or antibody fragments thereof against PA peptides from the infectious bacteria. In this and other embodiments, a method is provided which comprises providing a subject in need of immunization against an infectious bacteria or bacterial spores, a vaccine composition comprising particles of a diketopiperazine and an antigenic peptide of the infectious bacterium, and having the subject inhale the vaccine composition by oral inhalation; wherein the vaccine composition is provided in a single use disposable dry powder inhaler. In the methods, subjects can be immunized with a single administration of the vaccine composition; or a single administration of the vaccine composition and booster vaccine administrations can be administered at 4, 5, 6, 7, 8, 9, 10, 11, or 12 weeks, or longer after initial administration. In one embodiment, multiple booster vaccines can be administered up to 4 to 6 doses. Vaccine doses can vary depending on the subject, but can be greater than 0.10 mg of powder to about 10 mg of powder, such as 0.20 mg, 0.40 mg, 0.80 mg, 1 mg, 2 mg, 3 mg, 4 mg, 5 mg, 6 mg, 7 mg, 8 mg, 9 mg, or 10 mg. In some embodiments, the amount of peptide antigen in the composition can be at least 0.001 µg, at least 0.050 µg, at least 0.075 µg, or at least 0.10 µg of peptide in the vaccine composition.

In some embodiments disclosed herewith, the dry powder inhaler system comprises a predetermined mass flow balance within the inhaler. For example, a flow balance of approximately 10% to 70% of the total flow exiting the inhaler and into the patient is delivered by one or more dispensing ports, which airflow passes through the area containing the powder formulation, and wherein approximately 30% to 90% air flow is generated from other conduits of the inhaler. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the mouthpiece. In one embodiment, flow rates ranging from about 7 to 70 liters per minute result in greater than 75% of the container or the cartridge contents dispensed in fill masses between 1 and 30 mg. In certain embodiments, an inhalation system as described above can emit a respirable fraction/fill of a powder dose at percentages greater than 40%, greater than 50%, greater than 60%, or greater than 70% in a single inhalation.

In particular embodiments, an inhalation system is provided comprising a dry powder inhaler, a dry powder formulation comprising microparticles of fumaryl diketopiperazine having an FDKP trans isomer content between 45% and 65% and one or more than one active agents. In some aspects of this embodiment of the inhalation system, the dry powder formulation is provided in a unit dose cartridge. Alternatively, the dry powder formulation can be preloaded in the inhaler. In this embodiment, the structural configuration of the inhalation system allows the deagglomeration mechanism of the inhaler to produce respirable fractions greater than 50%; that is, more than half of the powder contained in the inhaler (cartridge) is emitted as particles of less than 5.8 µm. The inhalers can discharge greater than 85% of a powder medicament or vaccine contained within a container during dosing. In certain embodiments, the inhalers can discharge greater than 85% of a powder medicament or vaccine contained in a single inhalation. In one embodiment, the inhalers can discharge greater that 90% of the cartridge contents or container contents in less than 3 seconds at pressure differentials between 2 and 5 kPa with fill masses ranging up to 50 mg.

A method of immunizing a subject is also provided herewith comprising administering to a subject in need of immunization a therapeutically effective amount of a dry powder vaccine as described above and comprising an antigen, antibody, fragments thereof, or combinations thereof, and a diketopiperazine, including FDKP. In one embodiment, the antigen, antibody, or combinations thereof are for the treatment and prevention of a viral infection, including, influenza, and the dry powder vaccine is administered by inhalation and the inhalation system is configured to deliver a dose of the vaccine in a single inhalation in less than 1 seconds, or less than 2 seconds.

In an alternate embodiment, the dry powder formulation can be reconstituted with a solution or diluent, including phosphate buffered saline as an injectable formulation. In this embodiment, stable dry powder can be stored at room temperature up to about three months or longer, and reconstituted into a solution at the time of administration.

EXAMPLES

The following examples are included to demonstrate certain embodiments of the invention. It should be appreciated by those of skill in the art that the techniques disclosed in the examples elucidate representative techniques that function well in the practice of the present invention. However, those of skill in the art should, in light of the present disclosure, appreciate that many changes can be made in the specific embodiments that are disclosed and still obtain a like or similar result without departing from the spirit and scope of the invention. The injectable vaccine can be administered to a subject, for example, by an intramuscular injection.

Example 1

Preparation of Vaccine Compositions as an Inhalable Dry Material

In these experiments, a crystalline dry powder vaccine formulation was made using a hemagglutinin A3 antigen adsorbed onto preformed fumaryl diketopiperazine microparticles. FDKP powder was dissolved in a solution containing ammonium hydroxide and PS80 then precipitated with acetic acid solution and washed in water to form a suspension. A separately prepared solution (7.5 ml) containing HA3 in Tris-HCl buffer, sodium chloride and 1% glycerol was added to 3.3 g of the suspension with stirring at room temperature to yield a 5% HA3 content in the mixture. The resulting pH of the suspension was pH 4.1 and the suspension was pelletized in liquid nitrogen and lyophilized overnight under vacuum. Lyophilized FDKP-H3A powder was stored in a dessicator at ambient temperature. In an additional study, dry powder vaccine formulation was made as described above except that the suspension containing the FDKP-HA3 particles were instead sprayed dried to remove the solvents instead of pelletizing and lyophilizing. Lyophilized and spray-dried powders were tested for the presence of the HA3 in the formulation by various assays and methods including HPLC analysis (Waters Alliance 2695 HPLC equipped with a 2996 photodiode array detector and a Phenomenex, Aeris widepore 3.6 XB-C8, 15×2.10 mm column) and Column mobile phase used. Albumin at 1 mg/ml was used as standard using Mobile Phase A (0.1% TFA in water, pH 3.0±0.1; pH adjusted with 7% aqueous $NH_4OH$) and Mobile Phase B (0.1% TFA in CAN). Particle size distribution of the powder formulation was assessed using a dry powder inhaler (Mannkind Corp.) and Cascade Impaction apparatus using a cascade impactor (Andersen) at 4 kPa pressure differential.

The results from the HPLC analysis of the powder indicated that FDKP-HA3 formulation had a total protein content of 5.05% (w/w). Particle size distribution resulting from cascade impaction studies are presented in Table 1. The Data show that the dry powder made by spray-drying and lyophilization is effectively delivered out of the inhaler and more than 45% of the particles produced are within the respirable range.

TABLE 1

| Vaccine Formulation | % Respirable Fraction on Contents Delivered | % Respirable Fraction of Fill Contents | Total Amt. All Stages/Total Emptied | % Cartridge Emptying |
|---|---|---|---|---|
| Lyophilized FDKP-HA3 | 45.5 | 45.2 | 72.2 | 99.2 |
| Spray-Dried FDKP-HA3 | 53.8 | 53.1 | 65.4 | 98.7 |

Example 2

Immunization of Mice with FDKP-HA3 Inhalation Powder

Dry powder vaccine for inhalation containing HA3 prepared as described in Example 1 was used in these experiments.

Experimental Vaccine:

Powder composition of a rHA3 protein (derived from influenza A/Perth/2009 (H3N1). BALB/c mice were used and the mice were divided into groups. The first group, a group of female mice, 6-8 weeks old received powdered rHA3 vaccine (Vac-Powder) via the intra-pulmonary route (IPu) using an insufflation technique (Penn Century, Inc. Model DP-4M. A second group of mice received the equivalent dose of vaccine reconstituted into a liquid form (Vac-liquid), prior to inoculation via the intramuscular route (IM). The second group is used as a control to the intra-pulmonary route in the experiments. In addition, the third group of mice did not receive these materials and served as the untreated controls.

Dosage:

A Vac-Powder vaccine dose contains 0.5 mg of bulk powder with a rHA3 content of approximately 5% (e.g. 0.5 mg powder/0.025 mg rHA; 500 µg powder/25 µg rHA3). Pre- and post-insufflator device weights are measured to determine actual vaccine powder deliveries.

The Vac-liquid vaccine for intramuscular immunization was prepared by dissolving an equivalent amount of powder (0.5 mg powder/0.025 mg rHA3) with 40 µl of 100 mM Sodium Phosphate buffer, pH 7.24, and filtering the solution through a 0.22 µm filter prior to injection.

Immunization Regimen:

The mice received two doses of the corresponding treatment administered by the indicated route, two weeks apart. Animal handling and care were consistent with the current NIH "Guide for the Care and Use of Laboratory Animals" Federal and State Law and current operating procedures maintained by the Institution's Animal Facility. Mice were anesthetized prior to retro-orbital bleeding and for the insufflation procedure.

Experimental Groups:

Thirty six mice are randomized into three experimental units: 1) Control; 2) Vac-Powder-Intra-pulmonary powder vaccine, and 3) Vac-Liquid Intramuscular liquid form.

Treatments:

Three days prior to the initiation of the experiment, blood samples were collected from 5 mice per group (randomly selected) to assess pre-immunization immunological status. At day zero, all animals in each group received a first dose of vaccine or placebo, and two weeks later, all animal received a booster dose of vaccine or a second placebo treatment via the same route as the primary treatment. Two weeks after the booster dose, blood samples were collected from all animals (vaccine and controls) for appraising the immune response elicited by vaccine and control treatment. If deemed adequate, protective efficacy was be assessed by challenging all mice with $1 \times 10^6$ PFU of a homologous influenza virus [A/Perth/2009 (H3N1)].

Tables 2 and 3 summarize schedule of treatment and experimental details of the study, respectively.

Also, a dry powder vaccine as described in Table 3, Vac-Powder was reconstituted in PBS and administered intramuscularly to 12 mice to test the efficacy of the powder composition by another route of administration.

Assessment of Immunogenicity and Protective Efficacy:

Immunogenicity:

The level of serum antibody elicited by the rHA powder vaccine and control immunizations was evaluated by ELISA, micro-neutralization assay and hemagglutination inhibition (HAI). Serum samples from three mice of each group were pooled to assure sufficient material for the serological determinations.

If the elicited immune response is deemed adequate, animal in all groups are challenged with a homologous influenza virus [A/Perth/2009 (H3N1)].

Protective Efficacy:

The protective efficacy afforded by the rHA powdered vaccine or control immunizations was evaluated by challenging all animals with $1 \times 10^6$ PFU of influenza A/Perth/2009 (H3N1). Protection was assessed by measuring virus load in the upper and lower respiratory tract at days 3, 6, and 8 post-challenge in 4 mice per time point. Body weight measurements and clinical signs of disease were monitored daily until the last time point. Animals that experience greater than 20% body weight decrease or show severe symptoms of influenza such as labored breathing or paralysis were euthanized. In a separate group, mice were given an equivalent dose of a dry powder vaccine reconstituted into a liquid using 100 mM sodium phosphate buffer, pH 7.24 which was administered intramuscularly.

Immunization Results:

The results from immunization are shown in Table 4 below. The data are from mice immunized as described above receiving two doses of dry powder vaccine formulations as described herein and containing the Influenza virus HA3 antigen and delivered using an insufflation device (Penn Century). Mice were given a dose of the formulation at day 1 and a second dose 20 days after the initial vaccination. The data in Table 4 illustrate the amounts of HA3 and FDKP powder each mouse received at initial dose by insufflation followed by a booster dose 20 days after initial vaccination.

The data indicate that each mouse received an amount of the dry powder vaccine containing the HA3 antigen in amounts ranging from 2.5 µg to 30.35 µg by insufflation in both doses administered. The results from the animal studies indicate that the dry powder vaccine composition comprising fumaryl diketopiperazine particles and a viral rHA3 antigen stimulated the production of antibodies against the HA3 antigen in vivo as shown by a significant antibody response obtained from positive hemagluttination inhibition studies of sera obtained from dry powder vaccine intramuscularly immunized mice when compared to controls. Overall mice immunized with powderized rHA3 delivered either by insufflation (Vac-powder) or intramuscularly as a suspension (IM-Vac-powder) had reduced lung virus titers compared to intramuscular injections of saline solution [IM-PBS], standard VLPs administered intramuscularly (positive control), and lactose powder vaccine administered by insufflation.

TABLE 4

Penn Century discharge gravimetric data

| | | 1st insufflation 7-Sep | | | 2nd insufflation/Booster dose 27-Sep | | |
|---|---|---|---|---|---|---|---|
| | mouse ID | powder lot | powder delivered (mg) | HA3 delivered (µg) | powder lot | powder delivered (mg) | HA3 delivered (µg) |
| Vaccine delivery | 814 | Spray Dry | 0.261 | 13.05 | Lyo'd* | 0.493 | 24.65 |
| | 815 | Spray Dry | 0.103 | 5.15 | Lyo'd | 0.198 | 9.9 |
| | 816 | Spray Dry | 0.607 | 30.35 | Lyo'd | 0.369 | 18.45 |
| | 818 | Spray Dry | 0.193 | 9.65 | Lyo'd | 0.565 | 28.25 |
| | 819 | Lyo'd | 0.445 | 22.25 | Lyo'd | 0.373 | 18.65 |
| | 820 | Lyo'd | 0.464 | 23.2 | Lyo'd | 0.385 | 19.25 |
| | 821 | Spray Dry | 0.21 | 10.5 | Lyo'd | 0.126 | 6.3 |
| | 822 | Lyo'd | 0.155 | 7.75 | Lyo'd | 0.523 | 26.15 |
| | 823 | Lyo'd | 0.193 | 9.65 | Lyo'd | 0.299 | 14.95 |
| | 824 | Lyo'd | 0.412 | 20.6 | Lyo'd | 0.239 | 11.95 |
| | 825 | Lyo'd | 0.46 | 23 | Lyo'd | 0.338 | 16.9 |
| | 839 | Lyo'd | 0.412 | 20.6 | Lyo'd | 0.258 | 12.9 |
| | 840 | Lyo'd | 0.43 | 21.5 | Lyo'd | 0.176 | 8.8 |
| | 842 | Lyo'd | 0.402 | 20.1 | Lyo'd | 0.433 | 21.65 |
| | 843 | Spray Dry | 0.187 | 9.35 | Lyo'd | 0.447 | 22.35 |
| | 845 | Lyo'd | 0.19 | 9.5 | Lyo'd | 0.05 | 2.5 |

*Lyo'd denotes lyophilized powder

Example 3

Influenza Vaccine Administration

A 35 year old, healthy female who is needlephobic reports to her physician to receive her annual flu vaccine. Following examination, her physician provides her with a dry powder vaccine comprising 5 mg of powder containing fumaryl diketopiperazine microparticles and 50 µg of H3N1 antigen in a high resistance dry powder inhaler. The female patient places the mouthpiece of the inhaler in her mouth and deeply inhales the dry powder. After inhalation of the dry powder, the inhaler is safely discarded and the patient is discharged being immunized.

Vaccination Against *B. anthracis*:

A 19 year old healthy male who has enlisted into the military service reports for duty. Having found the enlisted serviceman healthy, the doctor provides a dry powder vaccine to the serviceman. The vaccination takes place in front of the doctor in which the serviceman orally inhales the vaccine from a dry powder inhaler in a single inhalation. The vaccine administered comprises a dry powder containing fumaryl diketopiperazine microparticles and 50 µg of PA peptide and is inhaled from a high resistance dry powder inhaler. A second dry powder inhaler is given to the serviceman to take a booster immunization 4 weeks later. The anthrax vaccine is administered annually.

Influenza Vaccine Administration:

A 55 year old, healthy female reports to her physician to receive her annual flu vaccine. Following examination, her physician provides her with a dry powder vaccine comprising 5 mg of powder containing fumaryl diketopiperazine microparticles and 50 µg of a combination of HA antigen and a neuraminidase inhibitor in a high resistance dry powder inhaler. The female patient places the mouthpiece of the inhaler in her mouth and deeply inhales the dry powder. After inhalation of the dry powder, the inhaler is safely discarded and the patient is discharged being immunized.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed is:

1. An influenza vaccine comprising a dry powder composition comprising a diketopiperazine and at least one of influenza virus-like particles, an antigenic protein, an antigenic peptide, fragments of said influenza virus-like particle, a subunit protein or multiple subunit proteins or fragments of said antigenic protein(s), fragments of said antigenic peptide, or combinations thereof.

2. The influenza vaccine of claim 1, wherein the virus-like particle comprises a hemagglutinin and/or a neuraminidase protein and/or a matrix protein, or peptide or fragments thereof.

3. The influenza vaccine of claim 1, wherein the antigenic protein or peptide is neuraminidase derived for influenza virus type A, B or C, or any subtype of influenza A, or fragments thereof or combinations thereof.

4. The influenza vaccine of claim 1, wherein the antigenic protein or peptide is hemagglutinin derived from influenza A, B or C or any subtype of influenza A, or fragments thereof, or combinations thereof.

5. The influenza vaccine of claim 4, wherein the antigenic protein or antigenic peptide is hemagglutinin A, or wherein the antigenic protein or subunit is another protein of the influenza virus such as NP, M1, M2, NS1, NS2, polymerase subunits PB1, PB2 or PA or fragments thereof or combinations thereof.

6. The influenza vaccine of claim 1, wherein the diketopiperazine is 3,6-bis-(N-X-4-aminobutyl)]-2,5-diketopiperazine.

7. The influenza vaccine of claim 6, wherein X is fumaryl, glutaryl, succinyl, maleyl, malonyl, or oxalyl.

8. The influenza vaccine of claim 1, wherein the diketopiperazine is 3,6-bis-(N-fumaryl-4-aminobutyl)]-2,5-diketopiperazine.

9. An influenza vaccine, comprising an inhalation system comprising a dry powder inhaler comprising a dry powder formulation comprising microparticles of 3,6-bis-(N-fumaryl-4-aminobutyl)]-2,5-diketopiperazine salt and an antigen selected from influenza virus protein consisting of hemagglutinin A or neuraminidase A, or other influenza protein and/or combinations thereof.

10. The influenza vaccine of claim 9, wherein the hemagglutinin A is a recombinant HA3 antigen.

11. The influenza vaccine of claim 9, wherein the dry powder inhaler is configured as a single use disposable inhaler for self-administration.

12. A method for immunizing a subject against an influenza virus infection, comprising administering to the subject a therapeutically effective amount of a dry powder vaccine comprising a diketopiperazine and a virus-like particle, an antigenic protein, an antigenic peptide, fragments of said virus-like particle, or a subunit protein or multiple distinct subunits proteins or fragments of said antigenic protein/s, fragments of said antigenic peptide, or combinations thereof, wherein the vaccine is self-administered by inhalation.

13. The method of claim 12, wherein the diketopiperazine is 3,6-bis-(N-X-4-aminobutyl)]-2,5-diketopiperazine.

14. The method of claim 13, wherein X is fumaryl, glutaryl, succinyl, maleyl, malonyl, or oxalyl.

15. The method of claim 14, wherein the diketopiperazine is 3,6-bis-(N-fumaryl-4-aminobutyl)]-2,5-diketopiperazine.

16. The method of claim 12, wherein the antigenic peptide is a recombinant HA3 antigen or fragment thereof.

17. A method of immunizing a subject against an influenza viral infection comprising, administering to said subject in need of immunization the influenza vaccine of claim 9.

18. The method of claim 17, further comprising providing a booster vaccine dose to said subject, said booster vaccine comprising the influenza vaccine of claim 9.

19. The method of claim 18, wherein said booster vaccine is administered within a month of administration of the initial dose.

20. The method of claim 19, wherein said booster vaccine is administered one week after administration of the initial dose.

* * * * *